(12) United States Patent
Woloszczuk et al.

(10) Patent No.: US 9,103,839 B2
(45) Date of Patent: Aug. 11, 2015

(54) METHOD OF DETERMINING EQUINE NT-PROBNP

(75) Inventors: Wolfgang Woloszczuk, Vienna (AT); Gerhard Hawa, Vienna (AT)

(73) Assignee: BIOMEDICA MEDIZINPRODUKTE GMBH & CO KG, Vienna (AT)

( * ) Notice: Subject to any disclaimer, the term of this patent is extended or adjusted under 35 U.S.C. 154(b) by 1077 days.

(21) Appl. No.: 12/530,122

(22) PCT Filed: Mar. 7, 2008

(86) PCT No.: PCT/AT2008/000084
§ 371 (c)(1),
(2), (4) Date: Sep. 4, 2009

(87) PCT Pub. No.: WO2008/106707
PCT Pub. Date: Sep. 12, 2008

(65) Prior Publication Data
US 2010/0136590 A1   Jun. 3, 2010

(30) Foreign Application Priority Data

Mar. 7, 2007  (AT) ..................................... 365/2007

(51) Int. Cl.
C07K 14/58   (2006.01)
C07K 16/26   (2006.01)
G01N 33/74   (2006.01)

(52) U.S. Cl.
CPC ................ *G01N 33/74* (2013.01); *C07K 14/58* (2013.01); *C07K 16/26* (2013.01); *C07K 2317/34* (2013.01); *G01N 2333/58* (2013.01); *G01N 2800/324* (2013.01); *G01N 2800/325* (2013.01)

(58) Field of Classification Search
CPC .... C07K 14/58; C07K 16/26; C07K 2317/34; G01N 33/74; G01N 2333/55; G01N 2800/324; G01N 2800/325
USPC .............. 435/6, 7.1, 7.5, 7.92, 7.93, 7.94, 28, 435/40.5, 40.52, 69.4, 69.6, 70.21, 331, 435/335, 287.2, 287.9, 975; 436/503, 504, 436/514, 516, 518, 536, 547, 548, 8, 169, 436/172, 807, 811; 530/300, 317, 328, 350, 530/387.9, 388.24, 388.25, 389.1, 389.2, 530/389.3, 391.1, 391.3, 806; 422/400, 422/420, 425, 430; 536/23.51
See application file for complete search history.

(56) References Cited

U.S. PATENT DOCUMENTS

| | | |
|---|---|---|
| 2004/0018577 A1 | 1/2004 | Emerson Campbell et al. ............................ 435/7.93 |
| 2004/0096919 A1 | 5/2004 | Davey et al. .................. 435/7.92 |
| 2005/0244902 A1* | 11/2005 | Gotze et al. ................... 435/7.92 |
| 2007/0161041 A1* | 7/2007 | Woloszczuk et al. .......... 435/7.1 |
| 2009/0286256 A1* | 11/2009 | Adamczyk et al. ............ 435/7.1 |

FOREIGN PATENT DOCUMENTS

| | | |
|---|---|---|
| EP | 0 648 228 B1 | 11/1998 |
| EP | 1 016 867 A1 | 7/2000 |
| EP | 1 100 830 B1 | 10/2003 |
| EP | 1 557 431 A1 | 7/2005 |
| FR | 2 843 396 A1 | 2/2004 |
| WO | WO 00/035951 | 6/2000 |
| WO | WO 03/087819 | 10/2003 |
| WO | WO 2006/027374 | 3/2006 |

OTHER PUBLICATIONS

Biondo et al., "Immunohistochemistry of atrial and brain natriuretic peptides in control cats and cats with hypertrophic cardiomyopathy," *Vet. Pathol.*, 40:501-506, 2003.

Coupal et al., "Photoaffinity-scan of bovine NPR-A by benzophenone probes derived from [N, C, rNAP (1-28)BNP32 (pBNP1)," *Proceedings of the 25th European Peptide Symposium*, Budapest, HU, pp. 572-573, Aug. 30-Sep. 4, 1998.

International Search Report and Written Opinion, issued in Int. App. No. PCT/AT2008/000084, mailed Jul. 2, 2008.

Jortani et al., "Strategies for developing biomarkers of heart failure," *Clin. Chem.*, 50:265-278, 2003.

Mifune et al., "Detection of immunoreactive atrial and brain natriuretic peptides in the equine atrium," *Anat. Embryol.*, 192:117-21, 1995.

Richter et al., "Equine cardiodilatin/ atrial natriuretic peptide. Primary structure and immunohistochemical localization in auricular cardiocytes," *Acta. Anat.*, 162:185-93, 1998.

\* cited by examiner

*Primary Examiner* — Gail R Gabel
*Assistant Examiner* — James L Grun
(74) *Attorney, Agent, or Firm* — Norton Rose Fulbright US LLP

(57) ABSTRACT

The invention relates to a method of determining equine NT-proBNP, or fragments thereof, comprising the steps of: providing an equine sample, contacting the sample with at least one antibody which specifically binds to equine NT-proBNP, and determining the presence and/or concentration of the equine NT-proBNP or fragments thereof existing in the sample.

22 Claims, 10 Drawing Sheets

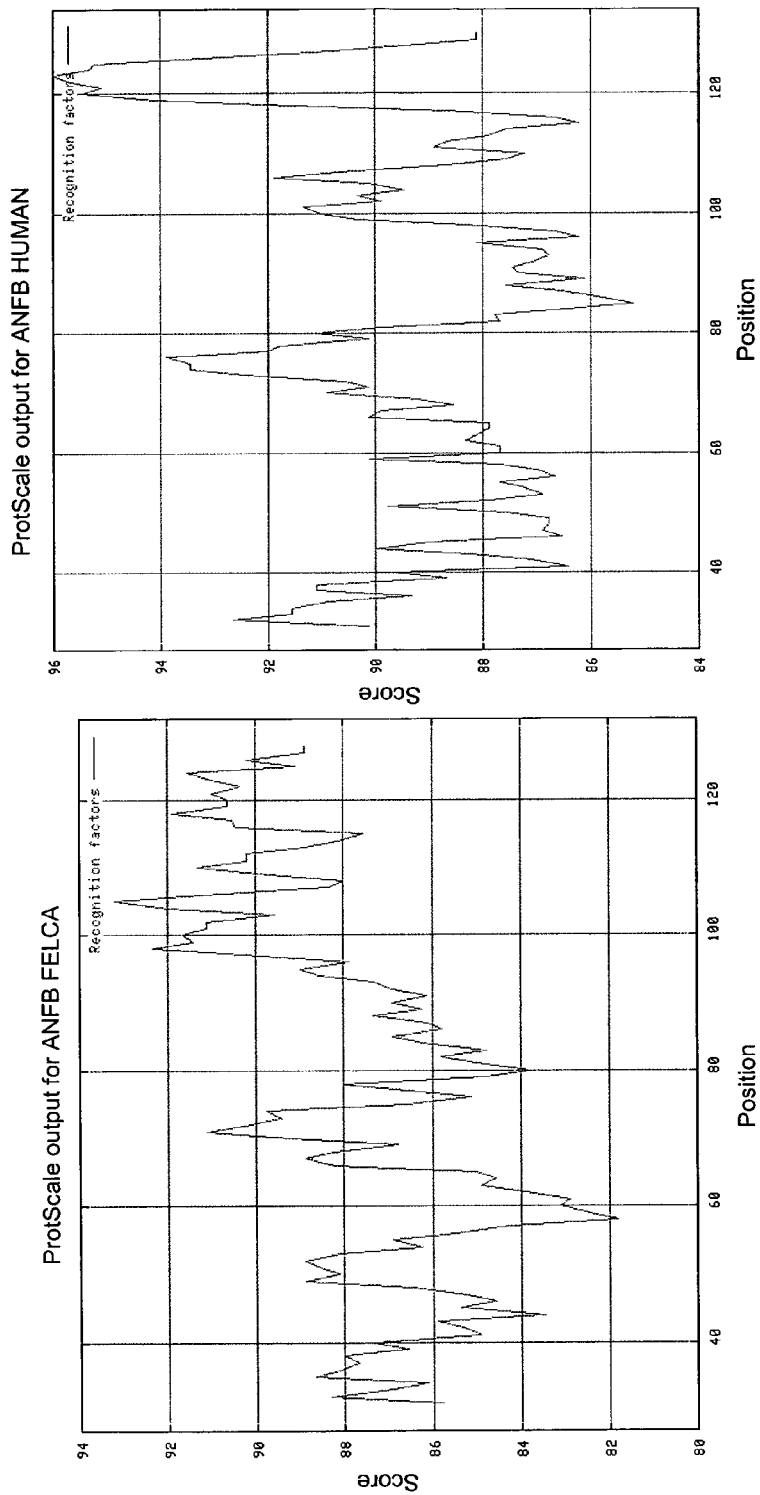
Fig.3 (Continuation)

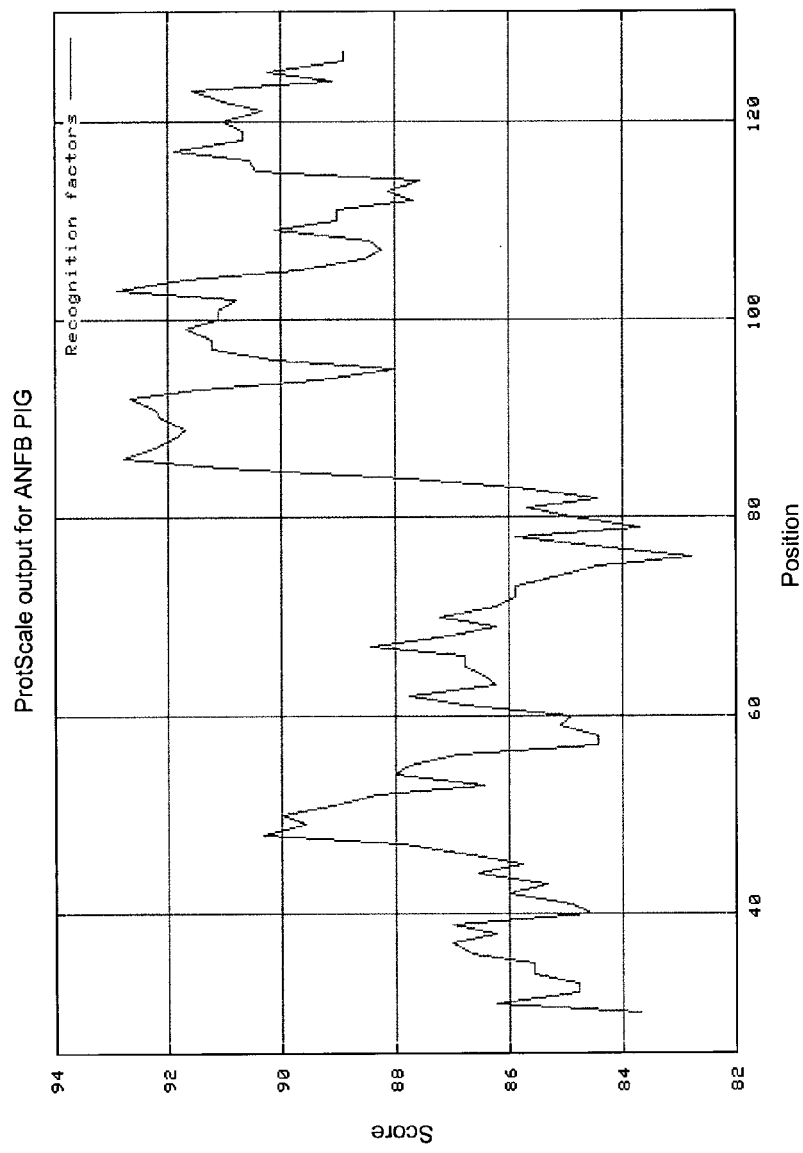
Fig.3 (Continuation)

Fig.8

SEQUENCE LISTING

```
<160> NUMBER OF SEQ ID NOS: 47

<210> SEQ ID NO 1
<211> LENGTH: 113
<212> TYPE: PRT
<213> ORGANISM: Equus caballus

<400> SEQUENCE: 1

Ser Pro Leu Gly Gly Arg Ser Tyr Pro Leu Gly Gly Leu Gly Pro Ala
1               5                   10                  15

Ser Glu Gln Ser Gly Ile Gln Glu Leu Leu Asp Arg Leu Gly Asp Ser
                20                  25                  30

Val Leu Glu Pro Gln Ala Glu Arg Met Thr Leu Glu Pro Leu Gln Gln
            35                  40                  45

Asp Arg Gly Pro Ala Glu Ala Ser Glu Thr Arg Gly Ala Ala Pro Thr
        50                  55                  60

Gly Val Leu Gly Pro Arg Thr Lys Val Leu Gln Ala Leu Arg Gly Leu
65                  70                  75                  80

Arg Ser Pro Lys Met Met Arg Asn Ser Gly Cys Phe Gly Arg Arg Leu
                85                  90                  95

Asp Arg Ile Gly Ser Phe Ser Gly Leu Gly Cys Asn Val Leu Arg Arg
            100                 105                 110

Tyr

<210> SEQ ID NO 2
<211> LENGTH: 106
<212> TYPE: PRT
<213> ORGANISM: Equus caballus

<400> SEQUENCE: 2

Tyr Pro Leu Gly Gly Leu Gly Pro Ala Ser Glu Gln Ser Gly Ile Gln
1               5                   10                  15

Glu Leu Leu Asp Arg Leu Gly Asp Ser Val Leu Glu Pro Gln Ala Glu
                20                  25                  30

Arg Met Thr Leu Glu Pro Leu Gln Gln Asp Arg Gly Pro Ala Glu Ala
            35                  40                  45
```

```
Ser Glu Thr Arg Gly Ala Ala Pro Thr Gly Val Leu Gly Pro Arg Thr
        50                  55                  60

Lys Val Leu Gln Ala Leu Arg Gly Leu Arg Ser Pro Lys Met Met Arg
65                  70                  75                  80

Asn Ser Gly Cys Phe Gly Arg Arg Leu Asp Arg Ile Gly Ser Phe Ser
                85                  90                  95

Gly Leu Gly Cys Asn Val Leu Arg Arg Tyr
            100                 105

<210> SEQ ID NO 3
<211> LENGTH: 12
<212> TYPE: PRT
<213> ORGANISM: Artificial
<220> FEATURE:
<223> OTHER INFORMATION: equine NT-proBNP fragment

<400> SEQUENCE: 3

Pro Leu Gly Gly Leu Gly Pro Ala Ser Glu Gln Ser
1               5                   10

<210> SEQ ID NO 4
<211> LENGTH: 12
<212> TYPE: PRT
<213> ORGANISM: Artificial
<220> FEATURE:
<223> OTHER INFORMATION: equine NT-proBNP fragment

<400> SEQUENCE: 4

Pro Ala Ser Glu Gln Ser Gly Ile Gln Glu Leu Leu
1               5                   10

<210> SEQ ID NO 5
<211> LENGTH: 12
<212> TYPE: PRT
<213> ORGANISM: Artificial
<220> FEATURE:
<223> OTHER INFORMATION: equine NT-proBNP fragment

<400> SEQUENCE: 5

Leu Leu Asp Arg Leu Gly Asp Ser Val Leu Glu Pro
1               5                   10

<210> SEQ ID NO 6
<211> LENGTH: 12
<212> TYPE: PRT
<213> ORGANISM: Artificial
<220> FEATURE:
<223> OTHER INFORMATION: equine NT-proBNP fragment

<400> SEQUENCE: 6

Ser Val Leu Glu Pro Gln Ala Glu Arg Met Thr Leu
1               5                   10

<210> SEQ ID NO 7
<211> LENGTH: 12
<212> TYPE: PRT
<213> ORGANISM: Artificial
<220> FEATURE:
<223> OTHER INFORMATION: equine NT-proBNP fragment

<400> SEQUENCE: 7

Pro Gln Ala Glu Arg Met Thr Leu Glu Pro Leu Gln
1               5                   10
```

-continued

```
<210> SEQ ID NO 8
<211> LENGTH: 12
<212> TYPE: PRT
<213> ORGANISM: Artificial
<220> FEATURE:
<223> OTHER INFORMATION: equine NT-proBNP fragment

<400> SEQUENCE: 8

Glu Pro Leu Gln Gln Asp Arg Gly Pro Ala Glu Ala
1               5                   10

<210> SEQ ID NO 9
<211> LENGTH: 12
<212> TYPE: PRT
<213> ORGANISM: Artificial
<220> FEATURE:
<223> OTHER INFORMATION: equine NT-proBNP fragment

<400> SEQUENCE: 9

Leu Gln Gln Asp Arg Gly Pro Ala Glu Ala Ser Glu
1               5                   10

<210> SEQ ID NO 10
<211> LENGTH: 12
<212> TYPE: PRT
<213> ORGANISM: Artificial
<220> FEATURE:
<223> OTHER INFORMATION: equine NT-proBNP fragment

<400> SEQUENCE: 10

Asp Arg Gly Pro Ala Glu Ala Ser Glu Thr Arg Gly
1               5                   10

<210> SEQ ID NO 11
<211> LENGTH: 12
<212> TYPE: PRT
<213> ORGANISM: Artificial
<220> FEATURE:
<223> OTHER INFORMATION: equine NT-proBNP fragment

<400> SEQUENCE: 11

Pro Ala Glu Ala Ser Glu Thr Arg Gly Ala Ala Pro
1               5                   10

<210> SEQ ID NO 12
<211> LENGTH: 12
<212> TYPE: PRT
<213> ORGANISM: Artificial
<220> FEATURE:
<223> OTHER INFORMATION: equine NT-proBNP fragment

<400> SEQUENCE: 12

Arg Gly Ala Ala Pro Thr Gly Val Leu Gly Pro Arg
1               5                   10

<210> SEQ ID NO 13
<211> LENGTH: 12
<212> TYPE: PRT
<213> ORGANISM: Artificial
<220> FEATURE:
<223> OTHER INFORMATION: equine NT-proBNP fragment

<400> SEQUENCE: 13

Leu Gly Pro Arg Thr Lys Val Leu Gln Ala Leu Arg
1               5                   10

<210> SEQ ID NO 14
```

```
<211> LENGTH: 12
<212> TYPE: PRT
<213> ORGANISM: Artificial
<220> FEATURE:
<223> OTHER INFORMATION: equine NT-proBNP fragment

<400> SEQUENCE: 14

Pro Arg Thr Lys Val Leu Gln Ala Leu Arg Gly Leu
1               5                   10

<210> SEQ ID NO 15
<211> LENGTH: 12
<212> TYPE: PRT
<213> ORGANISM: Artificial
<220> FEATURE:
<223> OTHER INFORMATION: equine NT-proBNP fragment

<400> SEQUENCE: 15

Leu Gln Ala Leu Arg Gly Leu Arg Ser Pro Lys Met
1               5                   10

<210> SEQ ID NO 16
<211> LENGTH: 12
<212> TYPE: PRT
<213> ORGANISM: Artificial
<220> FEATURE:
<223> OTHER INFORMATION: equine NT-proBNP fragment

<400> SEQUENCE: 16

Ser Pro Lys Met Met Arg Asn Ser Gly Cys Phe Gly
1               5                   10

<210> SEQ ID NO 17
<211> LENGTH: 12
<212> TYPE: PRT
<213> ORGANISM: Artificial
<220> FEATURE:
<223> OTHER INFORMATION: equine NT-proBNP fragment

<400> SEQUENCE: 17

Asp Arg Ile Gly Ser Phe Ser Gly Leu Gly Cys Asn
1               5                   10

<210> SEQ ID NO 18
<211> LENGTH: 27
<212> TYPE: DNA
<213> ORGANISM: Artificial
<220> FEATURE:
<223> OTHER INFORMATION: Primer

<400> SEQUENCE: 18
ctcctgctcc tcctsttctt gcacctg                                          27

<210> SEQ ID NO 19
<211> LENGTH: 12
<212> TYPE: PRT
<213> ORGANISM: Artificial
<220> FEATURE:
<223> OTHER INFORMATION: human NT-proBNP fragment

<400> SEQUENCE: 19

Pro Leu Gly Ser Pro Gly Ser Ala Ser Asp Leu Glu
1               5                   10

<210> SEQ ID NO 20
<211> LENGTH: 12
<212> TYPE: PRT
```

```
<213> ORGANISM: Artificial
<220> FEATURE:
<223> OTHER INFORMATION: murine NT-proBNP fragment

<400> SEQUENCE: 20

Pro Leu Gly Ser Pro Ser Gln Ser Pro Glu Gln Phe
1               5                   10

<210> SEQ ID NO 21
<211> LENGTH: 12
<212> TYPE: PRT
<213> ORGANISM: Artificial
<220> FEATURE:
<223> OTHER INFORMATION: rat NT-proBNP fragment

<400> SEQUENCE: 21

Pro Leu Gly Ser Pro Ser Gln Ser Pro Glu Gln Ser
1               5                   10

<210> SEQ ID NO 22
<211> LENGTH: 12
<212> TYPE: PRT
<213> ORGANISM: Artificial
<220> FEATURE:
<223> OTHER INFORMATION: porcine NT-proBNP fragment

<400> SEQUENCE: 22

Pro Leu Gly Gly Ala Gly Leu Ala Ser Glu Leu Pro
1               5                   10

<210> SEQ ID NO 23
<211> LENGTH: 12
<212> TYPE: PRT
<213> ORGANISM: Artificial
<220> FEATURE:
<223> OTHER INFORMATION: bovine NT-proBNP fragment

<400> SEQUENCE: 23

Pro Leu Gly Gly Pro Gly Pro Val Ser Glu Leu Pro
1               5                   10

<210> SEQ ID NO 24
<211> LENGTH: 12
<212> TYPE: PRT
<213> ORGANISM: Artificial
<220> FEATURE:
<223> OTHER INFORMATION: dog NT-proBNP fragment

<400> SEQUENCE: 24

Pro Leu Gly Gly Arg Ser Pro Ala Ser Glu Ala Ser
1               5                   10

<210> SEQ ID NO 25
<211> LENGTH: 12
<212> TYPE: PRT
<213> ORGANISM: Artificial
<220> FEATURE:
<223> OTHER INFORMATION: cat NT-proBNP fragment

<400> SEQUENCE: 25

Pro Leu Gly Gly Pro Gly Pro Ala Ser Glu Ala Ser
1               5                   10

<210> SEQ ID NO 26
<211> LENGTH: 12
<212> TYPE: PRT
<213> ORGANISM: Artificial
```

<220> FEATURE:
<223> OTHER INFORMATION: sheep NT-proBNP fragment

<400> SEQUENCE: 26

Pro Leu Gly Gly Pro Gly Ser Ala Ser Glu Leu Pro
1               5                   10

<210> SEQ ID NO 27
<211> LENGTH: 76
<212> TYPE: PRT
<213> ORGANISM: Homo sapiens

<400> SEQUENCE: 27

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75

<210> SEQ ID NO 28
<211> LENGTH: 63
<212> TYPE: PRT
<213> ORGANISM: Mus musculus

<400> SEQUENCE: 28

Tyr Pro Leu Gly Ser Pro Ser Gln Ser Pro Glu Gln Phe Lys Met Gln
1               5                   10                  15

Lys Leu Leu Glu Leu Ile Arg Glu Lys Ser Glu Glu Met Ala Gln Arg
            20                  25                  30

Gln Leu Leu Lys Asp Gln Gly Leu Thr Lys Glu His Pro Lys Arg Val
        35                  40                  45

Leu Arg Ser Gln Gly Ser Thr Leu Arg Val Gln Gln Arg Pro Gln
    50                  55                  60

<210> SEQ ID NO 29
<211> LENGTH: 61
<212> TYPE: PRT
<213> ORGANISM: Rattus rattus

<400> SEQUENCE: 29

His Pro Leu Gly Ser Pro Ser Gln Ser Pro Glu Gln Ser Thr Met Gln
1               5                   10                  15

Lys Leu Leu Glu Leu Ile Arg Glu Lys Ser Glu Glu Met Ala Gln Arg
            20                  25                  30

Gln Leu Ser Lys Asp Gln Gly Pro Thr Lys Glu Leu Leu Val Leu Arg
        35                  40                  45

Ser Gln Asp Ser Ala Phe Arg Ile Gln Glu Arg Leu Arg
    50                  55                  60

<210> SEQ ID NO 30
<211> LENGTH: 74
<212> TYPE: PRT
<213> ORGANISM: Felis catus

<400> SEQUENCE: 30

```
His Pro Leu Gly Gly Pro Gly Pro Ala Ser Glu Ala Ser Ala Ile Gln
1               5                   10                  15

Glu Leu Leu Asp Gly Leu Arg Asp Thr Val Ser Glu Leu Gln Glu Ala
            20                  25                  30

Gln Met Ala Leu Gly Pro Leu Gln Gln Gly His Ser Pro Ala Glu Ser
        35                  40                  45

Trp Glu Ala Gln Glu Glu Pro Pro Ala Arg Val Leu Ala Pro His Asp
50                  55                  60

Asn Val Leu Arg Ala Leu Arg Arg Leu Gly
65                  70
```

<210> SEQ ID NO 31
<211> LENGTH: 74
<212> TYPE: PRT
<213> ORGANISM: Equus caballus

<400> SEQUENCE: 31

```
Tyr Pro Leu Gly Gly Leu Gly Pro Ala Ser Glu Gln Ser Gly Ile Gln
1               5                   10                  15

Glu Leu Leu Asp Arg Leu Gly Asp Ser Val Leu Glu Pro Gln Ala Glu
            20                  25                  30

Arg Met Thr Leu Glu Pro Leu Gln Gln Asp Arg Gly Pro Ala Glu Ala
        35                  40                  45

Ser Glu Thr Arg Gly Ala Ala Pro Thr Gly Val Leu Gly Pro Arg Thr
50                  55                  60

Lys Val Leu Gln Ala Leu Arg Gly Leu Arg
65                  70
```

<210> SEQ ID NO 32
<211> LENGTH: 108
<212> TYPE: PRT
<213> ORGANISM: Homo sapiens

<400> SEQUENCE: 32

```
His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105
```

<210> SEQ ID NO 33
<211> LENGTH: 95
<212> TYPE: PRT
<213> ORGANISM: Mus musculus

<400> SEQUENCE: 33

```
Tyr Pro Leu Gly Ser Pro Ser Gln Ser Pro Glu Gln Phe Lys Met Gln
1               5                   10                  15

Lys Leu Leu Glu Leu Ile Arg Glu Lys Ser Glu Glu Met Ala Gln Arg
```

-continued

```
                 20                  25                  30

Gln Leu Leu Lys Asp Gln Gly Leu Thr Lys Glu His Pro Lys Arg Val
         35                  40                  45

Leu Arg Ser Gln Gly Ser Thr Leu Arg Val Gln Gln Arg Pro Gln Asn
     50                  55                  60

Ser Lys Val Thr His Ile Ser Ser Cys Phe Gly His Lys Ile Asp Arg
 65                  70                  75                  80

Ile Gly Ser Val Ser Arg Leu Gly Cys Asn Ala Leu Lys Leu Leu
                 85                  90                  95

<210> SEQ ID NO 34
<211> LENGTH: 61
<212> TYPE: PRT
<213> ORGANISM: Rattus rattus

<400> SEQUENCE: 34

His Pro Leu Gly Ser Pro Ser Gln Ser Pro Glu Gln Ser Thr Met Gln
 1               5                  10                  15

Lys Leu Leu Glu Leu Ile Arg Glu Lys Ser Glu Glu Met Ala Gln Arg
                 20                  25                  30

Gln Leu Ser Lys Asp Gln Gly Pro Thr Lys Glu Leu Leu Val Leu Arg
         35                  40                  45

Ser Gln Asp Ser Ala Phe Arg Ile Gln Glu Arg Leu Arg
     50                  55                  60

<210> SEQ ID NO 35
<211> LENGTH: 106
<212> TYPE: PRT
<213> ORGANISM: Sus sp.

<400> SEQUENCE: 35

His Pro Leu Gly Gly Ala Gly Leu Ala Ser Glu Leu Pro Gly Ile Gln
 1               5                  10                  15

Glu Arg Leu Leu Asp Arg Leu Arg Asp Arg Val Ser Glu Leu Gln Ala
                 20                  25                  30

Glu Arg Thr Asp Leu Glu Pro Leu Arg Gln Asp Arg Gly Leu Thr Glu
         35                  40                  45

Ala Trp Ala Arg Glu Ala Ala Pro Thr Gly Val Leu Gly Pro Arg Ser
     50                  55                  60

Ser Ile Phe Gln Val Arg Leu Gly Ile Arg Ser Pro Lys Thr Met Arg
 65                  70                  75                  80

Asp Ser Gly Cys Phe Gly Arg Arg Leu Asp Arg Ile Gly Ser Leu Ser
                 85                  90                  95

Gly Leu Gly Cys Asn Val Leu Arg Arg Tyr
                100                 105

<210> SEQ ID NO 36
<211> LENGTH: 103
<212> TYPE: PRT
<213> ORGANISM: Bos sp.

<400> SEQUENCE: 36

His Pro Val Gly Gly Pro Gly Val Ser Glu Leu Pro Gly Leu Gln
 1               5                  10                  15

Glu Leu Leu Asp Arg Leu Arg Asp Arg Val Ser Glu Leu Gln Ala Glu
                 20                  25                  30

Gln Leu Arg Val Glu Leu Pro Gln Gln Gly Gln Gly Leu Glu Glu Thr
         35                  40                  45
```

```
Trp Asp Ser Pro Ala Ala Pro Ala Gly Phe Leu Gly Pro His His
 50                  55                  60

Ser Ile Leu Arg Ala Leu Arg Pro Gly Lys Met Met Arg Asp Ser Gly
 65                  70                  75                  80

Cys Phe Gly Arg Arg Leu Asp Arg Ile Gly Ser Leu Ser Gly Leu Gly
                 85                  90                  95

Cys Asn Val Leu Arg Arg Tyr
            100

<210> SEQ ID NO 37
<211> LENGTH: 108
<212> TYPE: PRT
<213> ORGANISM: Canis lupus

<400> SEQUENCE: 37

His Pro Leu Gly Gly Arg Ser Pro Ala Ser Glu Ala Ser Gly Leu Trp
  1               5                  10                  15

Ala Val Gln Glu Leu Leu Gly Arg Leu Lys Asp Ala Val Ser Leu Glu
                 20                  25                  30

Gln Ala Glu Gln Leu Ala Leu Glu Pro Leu His Arg Ser His Ser Pro
             35                  40                  45

Ala Glu Ala Pro Glu Ala Gly Gly Thr Pro Arg Gly Val Leu Ala Pro
 50                  55                  60

His Asp Ser Val Leu Gln Ala Leu Arg Arg Leu Arg Ser Pro Lys Met
 65                  70                  75                  80

Met His Lys Ser Gly Cys Phe Gly Arg Arg Leu Asp Arg Ile Gly Ser
                 85                  90                  95

Leu Ser Gly Leu Gly Cys Asn Val Leu Arg Lys Tyr
            100                 105

<210> SEQ ID NO 38
<211> LENGTH: 106
<212> TYPE: PRT
<213> ORGANISM: Felis catus

<400> SEQUENCE: 38

His Pro Leu Gly Gly Pro Gly Pro Ala Ser Glu Ala Ser Ala Ile Gln
  1               5                  10                  15

Glu Leu Leu Asp Gly Leu Arg Asp Thr Val Ser Glu Leu Gln Glu Ala
                 20                  25                  30

Gln Met Ala Leu Gly Pro Leu Gln Gln Gly His Ser Pro Ala Glu Ser
             35                  40                  45

Trp Glu Ala Gln Glu Pro Pro Ala Arg Val Leu Ala Pro His Asp
 50                  55                  60

Asn Val Leu Arg Ala Leu Arg Arg Leu Gly Ser Ser Lys Met Met Arg
 65                  70                  75                  80

Asp Ser Arg Cys Phe Gly Arg Arg Leu Asp Arg Ile Gly Ser Leu Ser
                 85                  90                  95

Gly Leu Gly Cys Asn Val Leu Arg Arg His
            100                 105

<210> SEQ ID NO 39
<211> LENGTH: 103
<212> TYPE: PRT
<213> ORGANISM: Ovis sp.

<400> SEQUENCE: 39
```

-continued

```
His Pro Leu Gly Gly Pro Gly Ser Ala Ser Glu Leu Pro Gly Leu Gln
1               5                   10                  15

Glu Leu Leu Asp Arg Leu Arg Asp Arg Val Ser Glu Leu Gln Ala Glu
                20                  25                  30

Gln Leu Arg Val Glu Pro Leu Gln Gln Gly Gln Gly Leu Glu Glu Thr
            35                  40                  45

Trp Asp Ser Pro Ala Ala Pro Ala Gly Phe Leu Gly Pro His His
    50                  55                  60

Ser Leu Leu Gln Ala Leu Arg Gly Pro Lys Met Met Arg Asp Ser Gly
65                  70                  75                  80

Cys Phe Gly Arg Arg Leu Asp Arg Ile Gly Ser Leu Ser Gly Leu Gly
                85                  90                  95

Cys Asn Val Leu Arg Arg Tyr
            100
```

<210> SEQ ID NO 40
<211> LENGTH: 47
<212> TYPE: PRT
<213> ORGANISM: Artificial
<220> FEATURE:
<223> OTHER INFORMATION: fragment of an equine NT-proBNP variant

<400> SEQUENCE: 40

```
His Pro Leu Gly Gly Pro Gly Pro Ala Ser Glu Leu Pro Gly Leu Gln
1               5                   10                  15

Glu Leu Leu Asp Arg Leu Arg Asp Arg Val Ser Glu Leu Gln Ala Glu
                20                  25                  30

Gln Leu Ala Leu Glu Pro Leu Gln Gln Gly Gln Gly Leu Glu Glu
            35                  40                  45
```

<210> SEQ ID NO 41
<211> LENGTH: 47
<212> TYPE: PRT
<213> ORGANISM: Artificial
<220> FEATURE:
<223> OTHER INFORMATION: fragment of an equine NT-proBNP variant

<400> SEQUENCE: 41

```
His Pro Leu Gly Gly Pro Gly Pro Ala Ser Glu Leu Pro Gly Ile Gln
1               5                   10                  15

Glu Leu Leu Asp Arg Leu Arg Asp Arg Val Ser Glu Leu Gln Ala Glu
                20                  25                  30

Gln Leu Ala Val Glu Pro Leu Gln Gln Gly Gln Gly Leu Ala Glu
            35                  40                  45
```

<210> SEQ ID NO 42
<211> LENGTH: 47
<212> TYPE: PRT
<213> ORGANISM: Artificial
<220> FEATURE:
<223> OTHER INFORMATION: fragment of an equine NT-proBNP variant

<400> SEQUENCE: 42

```
His Pro Leu Gly Gly Pro Gly Pro Ala Ser Glu Leu Pro Gly Leu Gln
1               5                   10                  15

Glu Leu Leu Asp Arg Leu Arg Asp Arg Val Ser Glu Leu Gln Ala Glu
                20                  25                  30

Gln Leu Asp Leu Glu Pro Leu Gln Gln Gly Gln Gly Leu Thr Glu
            35                  40                  45
```

<210> SEQ ID NO 43
<211> LENGTH: 47
<212> TYPE: PRT
<213> ORGANISM: Artificial
<220> FEATURE:
<223> OTHER INFORMATION: fragment of an equine NT-proBNP variant

<400> SEQUENCE: 43

```
His Pro Leu Gly Gly Pro Gly Pro Ala Ser Glu Leu Pro Gly Ile Gln
1               5                   10                  15

Glu Leu Leu Asp Arg Leu Arg Asp Arg Val Ser Glu Leu Gln Ala Glu
            20                  25                  30

Gln Leu Asp Val Glu Pro Leu Gln Gln Gly Gln Gly Leu Glu Glu
        35                  40                  45
```

<210> SEQ ID NO 44
<211> LENGTH: 47
<212> TYPE: PRT
<213> ORGANISM: Artificial
<220> FEATURE:
<223> OTHER INFORMATION: fragment of an equine NT-proBNP variant

<400> SEQUENCE: 44

```
His Pro Leu Gly Gly Pro Gly Pro Ala Ser Glu Leu Pro Gly Leu Gln
1               5                   10                  15

Glu Leu Leu Asp Arg Leu Arg Asp Arg Val Ser Glu Leu Gln Ala Glu
            20                  25                  30

Gln Leu Arg Leu Glu Pro Leu Gln Gln Gly Gln Gly Leu Ala Glu
        35                  40                  45
```

<210> SEQ ID NO 45
<211> LENGTH: 47
<212> TYPE: PRT
<213> ORGANISM: Artificial
<220> FEATURE:
<223> OTHER INFORMATION: fragment of an equine NT-proBNP variant

<400> SEQUENCE: 45

```
His Pro Leu Gly Gly Pro Gly Pro Ala Ser Glu Leu Pro Gly Ile Gln
1               5                   10                  15

Glu Leu Leu Asp Arg Leu Arg Asp Arg Val Ser Glu Leu Gln Ala Glu
            20                  25                  30

Gln Leu Arg Val Glu Pro Leu Gln Gln Gly Gln Gly Leu Thr Glu
        35                  40                  45
```

<210> SEQ ID NO 46
<211> LENGTH: 545
<212> TYPE: DNA
<213> ORGANISM: Artificial
<220> FEATURE:
<223> OTHER INFORMATION: fragment of an equine cDNA of the pre-proBNP
       variant

<400> SEQUENCE: 46

```
ctcctgctcc tcctsttctt gcacctgtcg ccgctgggag gtcgttccta cccactgggc     60
ggcctcggcc ccgcctcgga acagtccgga atacaggagc tgctggaccg tttgggagac    120
tccgtcttgg agccgcaggc agagcggatg accctggagc cctccagca ggaccgtggc     180 cccgcagaag cctcggagac ccggggggca gcccctacgg tgtccttgg gccccgcacg     240 aaggtcctcc aggccctgcg gggactacga agccccaaga tgatgcgcaa ctcgggctgc    300
ttcgggcgga ggctagaccg gatcggctcc ttcagtggcc tgggctgcaa tgtgctgagg    360
```

-continued

```
aggtattaag aggaagtcct ggccgcagac aaccgcatct gactctccat caaccccctg    420
atcccctctg aagcaactcc tatttattta tttgtattta tttatttatt tagattgttt    480
tatataagat ggctcttacc tttgagcaca aatttgctgt ggtgaaataa aatcaatgtt    540
atggc                                                                545
```

<210> SEQ ID NO 47
<211> LENGTH: 179
<212> TYPE: PRT
<213> ORGANISM: Artificial
<220> FEATURE:
<223> OTHER INFORMATION: fragment of an equine pre-proBNP variant

<400> SEQUENCE: 47

Leu Leu Leu Leu Leu Phe Leu His Leu Ser Pro Leu Gly Gly Arg Ser
1               5                   10                  15
Tyr Pro Leu Gly Gly Leu Gly Pro Ala Ser Glu Gln Ser Gly Ile Gln
            20                  25                  30
Glu Leu Leu Asp Arg Leu Gly Asp Ser Val Leu Glu Pro Gln Ala Glu
        35                  40                  45
Arg Met Thr Leu Glu Pro Leu Gln Gln Asp Arg Gly Pro Ala Glu Ala
    50                  55                  60
Ser Glu Thr Arg Gly Ala Ala Pro Thr Gly Val Leu Gly Pro Arg Thr
65                  70                  75                  80
Lys Val Leu Gln Ala Leu Arg Gly Leu Arg Ser Pro Lys Met Met Arg
                85                  90                  95
Asn Ser Gly Cys Phe Gly Arg Arg Leu Asp Arg Ile Gly Ser Phe Ser
            100                 105                 110
Gly Leu Gly Cys Asn Val Leu Arg Arg Tyr Glu Glu Val Leu Ala Ala
        115                 120                 125
Asp Asn Arg Ile Leu Ser Ile Asn Pro Leu Ile Pro Ser Glu Ala Thr
    130                 135                 140
Pro Ile Tyr Leu Phe Val Phe Ile Tyr Leu Phe Arg Leu Phe Tyr Ile
145                 150                 155                 160
Arg Trp Leu Leu Pro Leu Ser Thr Asn Leu Leu Trp Asn Lys Ile Asn
                165                 170                 175
Val Met Ala

METHOD OF DETERMINING EQUINE NT-PROBNP

This application is a national phase application under 35 U.S.C. §371 of International Application No. PCT/AT2008/000084 filed 7 Mar. 2008, which claims priority to Austrian Application No. 365/2007 filed 7 Mar. 2007. The entire text of each of the above-referenced disclosures is specifically incorporated herein by reference without disclaimer.

The present invention relates to a method of determining NT-proBNP or fragments thereof in mammals.

Atrial natriuretic peptide (ANP), brain natriuretic peptide (BNP) and C-type natriuretic peptide (CNP) belong to a family of hormones which can be secreted from the atrium of the heart, the ventricles of the heart and the vascular endothelial cells.

C-terminally, all the natriuretic peptides have the same 17 amino acid ring structure connected by a disulfide bond. This part is responsible for their biological activity. At present, 3 receptors, the ANP-A receptor (specific to ANP and BNP), the ANP-B receptor (specific to CNP and ANP) and the clearance receptor have been characterised. BNP has first been isolated from porcine brain and has later on also been found in the porcine heart. It has already been described in the literature that the natriuretic peptides protect the organism against an excess of liquid and high blood pressure. The biological, biochemical and pathophysiological role of the natriuretic peptides has already been extensively described in review publications. Nowadays, the value of the natriuretic peptides as a serum marker for diagnostics and therapy control of heart diseases in humans is well documented.

In humans, the mature form of the BNP which is mainly secreted from the ventricle forms from a high-molecular prestage, the proBNP (1-108). The physiologically active C-terminal peptide, proBNP (77-108), also termed BNP-32, consists of 32 amino acids, the N-terminal form which circulates in plasma consists of 76 amino acids (NT-proBNP(1-76)). Furthermore, also the fragments 8-29 and 31-57 of pre-proBNP have been described, wherein particularly the determination of the fragment 8-29 for measuring the NT-proBNP 1-76 provide analogous clinical data.

Heart diseases play an important role not only in humans, also animals, especially pets, such as dogs and cats, or useful animals, such as horses, are afflicted with these diseases. Horses suffering from heart diseases generally are not very fit, they sweat quickly, their pulse is increased, they are short of breath or have a fever. Approximately 0.3% of all the horses have a congenital heart defect, their arteries can transport less oxygen than in the healthy state. In most cases, however, heart problems develop in the course of life, cardiac arrythmias occur frequently, yet are mostly normal in the resting state. Pathological cardiac arrhythmias are a sign of a myocardial damage that may be caused by lack of oxygen or by infections. Inflammations of the myocardium are called myocarditis. If the chemical structure of the fibres of the myocardium changes, the heart will no longer be able to appropriately pump blood, and one speaks of myocardoses. Inflammations of the endocardium are triggered by bacteria reaching the heart through the blood, e.g. via inflamed hoofs or joints. In case of a dropsy of the pericardium, water enters the pericardium through the walls of the blood vessels. As a rule, non-treatment of cardiac problems will result in cardiac insufficiency. In slight cases, circulation will have a balancing effect, in severe cases, heart failure is to be expected. In horses suffering from a valve defect of the right half of the heart, blood retained in organs will lead to cirrhosis of the liver. Heart diseases are diagnosed by veterinarians by means of ausculation, ultrasonics or ECG. Initially, the horse should not be subjected to any stress, and ideally, it should be housed in an open stable or in an external horsebox so that the heart will be supplied with a large amount of oxygen. The curing or treatment, respectively, of heart diseases may take a very long time, a therapy will take 4-6 weeks at any event. Some horses can be cured permanently, others will have a relapse when medication is discontinued. However, even in case of curing, maximum performance can no longer be demanded from the horse. Since the heart is capable of initially balancing out dysfunctions by working harder, such an illness will remain undetected in most cases, with the consequence that the state of the heart will deteriorate due to the increased exertion of the heart. The symptoms resulting from heart diseases, such as fatigue, circulatory insufficiency, weariness in most cases will be recognizable when the animal's heart is no longer able to compensate for the weakness. In such a case, the heart disease will already have progressed so far that complete curing will hardly be possible. Diagnosing heart diseases in horses as early as possible would, therefore, be of great importance and could obviate irreparable damage or even prevent horses used in sports from having to be irrevocably barred from participating in sports involving races and tournaments.

Chronic changes in the heart valve and the myocardium are not curable as a rule, yet further progression of the heart disease can be slowed by the use of medicaments. Also for this reason, an early diagnosis of a developing heart disease is important. As a routine, mainly physical methods are used for this purpose, such as auscultation of the heart sounds, the recording of an electrocardiogram, X-ray and ultrasonic examinations. These examination methods primarily have the drawback that they can be carried out only after an already visible or audible heart damage is directly detectable. Moreover, physical examination methods require suitable and mostly expensive devices for making an appropriate diagnosis.

On the whole, the heart diseases of the horse are highly similar to analogous diseases in humans.

In many heart diseases, such as, e.g., cardiac insufficiency, dilated cardiomyopathy, hypertrophic cardiomyopathy, left ventricular hypertrophy and dysfunction, BNP is released. This hormone causes the secretion of liquid via the kidneys and, thus, regulates the cardiovascular system. Since this peptide is produced in the heart and is increasingly produced if the heart is overstressed and congested, detection of the BNP level in blood is a suitable means for assessing cardiac insufficiency.

BNP, also like other natriuretic peptides, plays an important part in regulating the water balance and the blood pressure. If the heart wall is stretched, it releases more BNP, resulting in a secretion of sodium and liquid via the kidney, and in a dilation of the blood vessels which, in sum, are capable of lowering the blood pressure and the filling of the heart. BNP is synthesized by the cells of the heart muscle as proBNP which, finally, is cleaved into N-terminal proBNP and BNP. Both parts of the BNP are secreted into the blood and can be detected therein.

Heart diseases in animals are, i.a., dealt with in the following relevant publications: Bright J M and Cali J V, J Am Vet Med Assoc 2000, 216:1110-4; Guglielmini C, Vet Res Commun 2003, 27 Suppl 1:555; Boswood A et al., J Small Anim Pract 2003, 44:104-8; Takemura N et al., J Vet Med Sci 2003, 65:1265-7; MacDonald K A et al., J Vet Intern Med 2003, 17:172-7; Greco D S et al., Can Vet J 2003, 44:293-7; Monnet E et al., J Am Vet Med Assoc 1997, 211:569-72; Hamlin R L et al., J Vet Intern Med 1996, 10:85-7; Gaschen L et al., J Vet Intern Med 1999, 13:346-56.

A plurality of methods are already known in the prior art by means of which human proBNP, or the fragments thereof, respectively, can be detected in the serum of an individual. EP 0 648 228 B1, WO 03/87819 and FR 2 843 396 may be mentioned here by way of example.

In US 2004/0018577, an immunoassay has been disclosed which comprises at least three antibodies which are all capable of binding to different epitopes of an analyte. The analytes to be detected here particularly relate to the detection of markers regarding heart diseases, wherein i.a. also BNP and proBNP can be detected.

Biondo A. W. et al. (Vet. Pathol. 2003, 40(5):501-506) describe a method of-detecting ANP and BNP in cats by means of polyclonal antibodies which are directed against a peptide of ANP comprising the amino acids 1 to 28, and against a peptide comprising the amino acids 43 to 56 of proBNP, respectively.

In EP 1 016 867 A1, an immunoassay for the detection of preproBnP in mammals has been described. Here, antibodies are used which are directed against peptides comprising the amino acids 27 to 102, 73 to 102 and 27 to 64 of human BNP.

Jortani S. A. et al. (Clin. Chem. 2003, 50(2):265-278) describe the use of BNP and its prepro- and pro-forms as possible markers for heart diseases. This article does not mention any preferred peptide regions of BNP which would be suitable to detect heart diseases in horses.

In WO 2000/35951, several peptides have been disclosed, against which antibodies can be produced which are suitable in a method of diagnosing heart diseases. Here, three peptides comprising the amino acids 1 to 13, 37 to 49, and 65 to 76 of the human Nt-pro-BNP protein are disclosed which may also be employed for the production of antibodies that are directed against these peptides.

In WO 2006/027374 A, specific BNP tests for dogs and cats have been disclosed. It has been shown that by means of the antibodies disclosed there, BNP could also be detected in some other animals, yet a specific detection of horse-BNP could not be provided so far.

In Mifune H et al. (Anat. Embryol. (Berl) 192 (1995): 117-21), a method of detecting immunoreactive ANP and BNP peptides in the atrium of horses' hearts has been described.

In EP 1 557 431 A1, a method of quantifying human BNP has been disclosed in which antibodies directed against the epitopes comprising the amino acid residues 5-13, 1-10, 15-25 and 17-32 of human BNP are used.

Richter R. et al. (Acta Anat (Basel), 162 (1998):185-93) describe the localisation of ANP in the hearts of horses.

Furthermore, several test kits for the detection of human proBNP and its fragments, respectively, are on the market (e.g. from Roche and Biomedica). Nevertheless, there is no known method by means of which proBNP can be specifically determined in equine samples. Therefore, and on account of the cost-intensive and complex physical examinations of horses, it is an object of the present invention to provide suitable means for determining proBNP, and its fragments, respectively, in samples from horses. In particular, a timely diagnosis of a beginning heart disease shall be enabled therewith.

Accordingly, the present invention relates to a method of determining equine NT-proBNP or fragments thereof, comprising the steps of:

providing an equine sample,
    contacting the sample with at least one antibody which specifically binds to equine NT-proBNP, and
    determining the presence and/or concentration of the equine NT-proBNP or fragments thereof existing in the sample.

With the present invention, the determination of equine NT-proBNP is provided in that specific antibodies against this species are disclosed. In this way, an efficient and early diagnosis of heart diseases in a horse can be achieved which is highly relevant.

Preferably, in the determination of equine NT-proBNP or fragments thereof, the at least one antibody binds to an (of course, horse-specific) NT-proBNP-epitope from SEQ ID No. 1, in particular to an epitope selected from the epitopes with the sequences PLGGLGPASEQS (SEQ ID No. 3), PASEQSGIQELL (SEQ ID No. 4), LLDRLGDSVLEP (SEQ ID No. 5), SVLEPQAERMTL (SEQ ID No. 6), PQAERMTLEPLQ (SEQ ID No. 7), EPLQQDRGPAEA (SEQ ID No. 8), LQQDRGPAEASE (SEQ ID No. 9), DRGPAEASETRG (SEQ ID No. 10), PAEASETRGAAP (SEQ ID No. 11), RGAAPTGVLGPR (SEQ ID No. 12), LGPRTKVLQALR (SEQ ID No. 13), PRTKVLQALRGL (SEQ ID No. 14) or LQALRGLRSPKM (SEQ ID No. 15).

Preferably, in the determination of equine NT-proBNP or fragments thereof, at least one NT-proBNP-antibody is additionally used which is not specific to equine NT-proBNP.

According to a preferred embodiment of the method according to the invention, at least one antibody is additionally used which is specific to equine pre-proBNP, in particular an antibody which specifically binds to at least one epitope from SEQ ID No. 1, selected from the epitopes with the sequences SPKMMRNSGCFG (SEQ ID No. 16) or DRIGSFSGLGCN (SEQ ID No. 17).

It is pointed out that the equine NT-proBNP- and proBNP-sequences, respectively, are mentioned by way of example for the entire horse family, whereby individual amino acids in the proBNP-sequences of animals of other genera of this family deviating from the sequences disclosed herein also are included by the sequences disclosed herein, as long as these deviating amino acids do not relate to the epitopes of the antibodies disclosed herein in a manner that a specific binding is no longer rendered possible. The amino acid sequences which are disclosed herein for the other species have been published in public data bases.

The samples used in the method according to the invention comprise liquid samples, such as, e.g., blood, urine, yet also tissue samples, such as, e.g., tissue sections of the cardiac musculature or of the brain. As required, the samples may be appropriately prepared e.g. so as to facilitate or render possible the later contacting of the sample with the antibodies of the invention. Thus, fractions containing proBNP, NT-proBNP, or fragments thereof, respectively, may be provided from blood samples, or tissue samples may, e.g., be homogenized and likewise be separated from non-proteinaceous fractions.

The binding of at least one antibody to an epitope of the equine NT-proBNP in the sample means that the antibody is capable of binding an epitope in a defined sequence region of a specific protein, this antibody not being capable of specifically binding epitopes of the protein externally of the defined region.

According to the invention, an antibody which is capable of binding a horse-specific epitope may be used to determine NT-proBNP and proBNP or fragments thereof. Nevertheless, it may be advantageous to use several (e.g. two, three, four or five) antibodies which are capable of binding different epitopes of the NT-proBNP.

The presence and/or the concentration of the equine NT-proBNP or fragment thereof existing in the sample may be determined by methods known in the prior art. By way of example, carrying out enzyme immunoassays (e.g. ELISA) in liquid samples, or immunohistochemical methods in tissue samples, respectively, should be mentioned here.

"Antibodies" according to the present invention also comprise fragments of antibodies capable of recognizing an epitope according to the invention. Thus, an antibody may, e.g., merely exist of the F(ab) portion which has the antigen-binding site. These antibody fragments may further be part of a bispecific antibody or of a heterominibody (cf. e.g. EP 1 100 830 B1).

"NT-proBNP or fragments thereof" according to the invention comprise all the NT-proBNP fragments which are formed in vivo or which are produced in vitro (e.g. by admixing a sample with protease or chemical substances, such as CNBr) and which have the epitopes according to the invention.

In a method according to the present invention, several antibodies capable of specifically binding several different epitopes on equine proBNP may be used. For this reason, at least one antibody which is capable of binding to at least one epitope can be used according to the invention. Furthermore, it should be mentioned here that the amino acid regions indicated here need not have only one epitope, but may also comprise several epitopes, depending on their size. Thus, the method according to the invention comprises the use of a combination of several antibodies capable of specifically binding to at least one epitope.

According to a preferred embodiment, the at least one antibody is polyclonal and/or monoclonal. Of course, according to the invention also functional variations of complete antibodies, their fragments or derivatives are subsumed under the term "antibody" by the person skilled in the art, or understood to be means equivalent to the antibodies.

The antibodies employed in a method according to the invention may be both polyclonal and also monoclonal. For producing these antibodies, peptide fragments comprising the amino acid regions disclosed herein of the equine proBNP are used. These peptide fragments may either be produced synthetically (Merrifield R. P., 1963, J Am. Chem. Soc 85, 2000, 149), recombinantly or by chemical or enzymatic degradation of proBNP of recombinant or native origin. Depending on their size, the peptides recovered therefrom will be bound to an immunogenic carrier (e.g. KLH) or be directly used for producing polyclonal or monoclonal antibodies (e.g. Köhler G. and Milstein C., 1975, Nature 256:495; Galfre et al., 1977, Nature 266:550). According to the invention, the antibodies may also be recombinantly produced. Methods of producing recombinant antibodies are sufficiently known to the person skilled in the art (cf., e.g., Sambrook et al., Molecular Cloning, A Laboratory Manual, Cold Spring Harbor, Laboratory Press, 2001).

According to a further preferred embodiment, at least one further antibody binds to the at least one antibody or to the at least one epitope, whereby, e.g., the test according to the invention can be carried out as a sandwich assay.

The binding of a further antibody to the at least one antibody makes it possible to determine the latter and, indirectly, the epitope bound to the at least one antibody, qualitatively, and quantitatively, respectively. If the at least one further antibody binds to the at least one epitope, it is possible—via an enzyme immunoassay—to qualitatively and quantitatively determine the binding of the at least one antibody to the at least one epitope if, e.g., the at least one antibody is immobilized on a solid phase.

Preferably, the at least one antibody and/or the at least one further antibody is labelled.

In this case, the at least one antibody and/or the at least one further antibody is labelled by an enzyme, such as peroxidase, in particular horseradish peroxidase, biotin, fluorescent dye, in particular fluoresceine (FITC, DFTF), R-phycoerythrin (PE), peridinium-chlorophyll-protein (PerCP) and tandem conjugates, such as PE-Cy5 or PE-Texas Red, gold colloid or radionuclides.

By labelling one of the two antibodies, it is possible to determine by a secondary reaction or to also determine directly the presence and concentration, respectively, of the labelled antibody bound to the at least one epitope. The antibodies themselves could, in turn, be detected by protein A conjugates (e.g. protein A gold conjugate).

According to a preferred embodiment, the at least one antibody or the at least one further antibody is bound to a solid phase.

By said binding of the at least one antibody or of the at least one further antibody, antibody chips, coated microtiter plates or lateral flow devices, e.g., can be produced which can be employed in a plurality of methods.

Preferably, the determination of equine proBNP or of fragments thereof is carried out by a method selected from the group consisting of radioimmunoassay, immunobinding assay, Western blot, immunohistochemistry, enzyme-immunoassay, lateral flow device (LFD, test strips) and combinations thereof.

The above-mentioned methods are sufficiently known to the person skilled in the art. A review of these methods may, e.g., be found in "Bioanalytik" (Lottspeich and Zorbas, Spektrum Verlag 1998). Lateral flow devices (LFD, test strips) have been disclosed in WO 02/059567, e.g.

According to a further aspect, the present invention also relates to antibodies or antibody mixtures specifically binding to an equine NT-proBNP. According to the invention, "specifically binding" means that by these antibodies, the equine form of the protein is specifically recognized and that these antibodies do not bind to proBNP of other species. In this case, it is sufficient if the antibodies exhibit this specificity under certain conditions easily determinable by the person skilled in the art, even if under less stringent conditions (in the antigen/antibody binding assay) this specificity is not present. In particular, by "specific" according to the present invention it is meant that the antibody or antibody mixture, respectively, according to the invention (e.g. the polyclonal antibody preparation or the mixture of monoclonal antibodies which recognize different epitopes) is capable of distinguishing equine NT-proBNP from human, murine, rat, porcine, bovine, canine, feline or sheep-proBNP in a binding assay (i.e., enter into a different binding, or bind equine preBNP exclusively, respectively).

Preferably, the antibodies or the antibody mixture according to the invention specifically bind(s) to at least one epitope from SEQ ID No. 1, selected from the epitopes with the sequences PLGGLGPASEQS (SEQ ID No. 3), PASEQS-GIQELL (SEQ ID No. 4), LLDRLGDSVLEP (SEQ ID No. 5), SVLEPQAERMTL (SEQ ID No. 6), PQAERMTLEPLQ (SEQ ID No. 7), EPLQQDRGPAEA (SEQ ID No. 8), LQQDRGPAEASE (SEQ ID No. 9), DRGPAEASETRG (SEQ ID No. 10), PAEASETRGAAP (SEQ ID No. 11), RGAAPTGVLGPR (SEQ ID No. 12), LGPRTKVLQALR (SEQ ID No. 13), PRTKVLQALRGL (SEQ ID No. 14), LQALRGLRSPKM (SEQ ID No. 15), SPKMMRNSGCFG (SEQ ID No. 16) or DRIGSFSGLGCN (SEQ ID No. 17). The specific binding to the horse-specific epitopes mentioned herein is achieved by the antibodies according to the invention preferably in larger polypeptides, primarily in equine pre-proBNP, proBNP, NT-proBNP or BNP. In this case, the antibodies according to the invention do not enter into any significant bindings with corresponding homologous polypeptides of other species, at least not under sufficiently stringent conditions (i.e. such conditions as are commonly used in clinical immunodiagnosing methods of BNP. The antibodies according to the invention are preferably produced by epitope-specific affinity chromatography or as epitope-specific monoclonal antibodies (in each case by using epitope mapping).

According to a further aspect, the present invention relates to a polypeptide with an amino acid sequence according to SEQ ID. No.1 or specific fragments thereof, in particular amino acids 8 to 113, 8 to 81 and 82 to 113 of SEQ ID No. 1. The amino acids 1 to 7 are no longer present in pre-proBNP (signal sequence); with amino acid 82 (S), the mature equine BNP hormone starts. A "specific" fragment of SEQ ID No. 1 is a fragment which differs by at least one amino acid residue from known pre-pro-BNP sequences and comprises at least 7, preferably at least 8, in particular at least 10 amino acids. Particularly preferred inventive fragments comprise preferably one or more epitopes selected from the group consisting of PLGGLGPASEQS (SEQ ID No. 3), PASEQSGIQELL (SEQ ID No. 4), LLDRLGDSVLEP (SEQ ID No. 5), SVLEPQAERMTL (SEQ ID No. 6), PQAERMTLEPLQ (SEQ ID No. 7), EPLQQDRGPAEA (SEQ ID No. 8), LQQDRGPAEASE (SEQ ID No. 9), DRGPAEASETRG (SEQ ID No. 10), PAEASETRGAAP (SEQ ID No. 11), RGAAPTGVLGPR (SEQ ID No. 12), LGPRTKVLQALR (SEQ ID No. 13), PRTKVLQALRGL (SEQ ID No. 14), LQALRGLRSPKM (SEQ ID No. 15), SPKMMRNSGCFG (SEQ ID No. 16) or DRIGSFSGLGCN (SEQ ID No. 17).

Therefore, the present invention also relates to a polypeptide with an amino acid sequence selected from the sequences PLGGLGPASEQS (SEQ ID No. 3), PASEQSGIQELL (SEQ ID No. 4), LLDRLGDSVLEP (SEQ ID No. 5), SVLEPQAERMTL (SEQ ID No. 6), PQAERMTLEPLQ (SEQ ID No. 7), EPLQQDRGPAEA (SEQ ID No. 8), LQQDRGPAEASE (SEQ ID No. 9), DRGPAEASETRG (SEQ ID No. 10), PAEASETRGAAP (SEQ ID No. 11), RGAAPTGVLGPR (SEQ ID No. 12), LGPRTKVLQALR (SEQ ID No. 13), PRTKVLQALRGL (SEQ ID No. 14), LQALRGLRSPKM (SEQ ID No. 15), SPKMMRNSGCFG (SEQ ID No. 16) or DRIGSFSGLGCN (SEQ ID No. 17).

According to a preferred embodiment, the inventive polypeptide is chemically synthesized or isolated from a sample, or recombinantly produced, respectively.

In order to appropriately produce the epitope from a peptide which has been isolated from a sample or which has been produced recombinantly, said peptide can be further processed by enzymatic or chemical methods known per se. The polypeptides according to the invention may also be provided as conjugates with further molecules, preferably with further molecules at the N- or C-terminus of the peptides, in particular with further polypeptides which are not naturally connected to the polypeptides of the invention.

A further aspect of the present invention relates to the use of an, antibody or an antibody mixture according to the invention for determining equine NT-proBNP or fragments thereof in a method according to the invention.

The peptides of the invention may be used in labelled form in competitive immunoassays.

Preferably, the peptides according to the present invention are used for producing an antibody or an antibody mixture.

Moreover, the peptides according to the present invention are used as a positive control or as a standard for concentration determinations in a method according to the invention.

A further aspect of the present invention relates to a kit for determining equine NT-proBNP or fragments thereof, comprising at least one antibody or at least one antibody mixture according to the invention, means for the qualitative and/or quantitative detection of a binding of the at least one antibody or of the at least one antibody mixture to equine NT-proBNP or to fragments thereof, and optionally peptides according to the invention (i.e. equine proBNP or fragments thereof) as a positive control or a standard for a concentration determination.

According to the invention, the kit may comprise at least one further antibody.

This additional antibody has an avidity to the at least one antibody or also to the at least one epitope.

According to a preferred embodiment, the at least one antibody and/or the at least one further antibody is labelled.

Preferably, said labelling comprises enzymes, such as peroxidases, in particular horseradish peroxidase, biotin, fluorescent dyes, in particular fluoresceine (FITC, DFTF), R-phycoerythrin (PE), peridinium-chlorophyll-protein (PerCP) and tandem conjugates, such as PE-Cy5 or PE-Texas Red, gold colloid or radionuclides.

A further aspect of the present invention relates to the use of an inventive kit in a method of determining equine proBNP.

According to a further aspect, the present invention relates to a method of recombinantly producing the polypeptides of the invention, wherein a nucleic acid coding for these polypeptides is introduced into a suitable host organism, the polypeptides are expressed by the host in a manner known per se, and the expressed polypeptides are recovered. These methods, including suitable hosts, expression systems and method of recovering the polypeptides as such are known to the person skilled in the art.

On the other hand, the polypeptides of the invention can also be chemically synthesized, preferably via the solid phase method (Merryfield). Also for this, a store of methods known per se is available to the person skilled in the art.

The present invention also relates to the use of the antibodies of the invention for diagnosing heart diseases in a horse. In this case, the antibodies may be used in the set-ups known for humans. The inventive polypeptides may also be used, e.g. as standard, comparative sample, or for titrating not yet reacted antibodies.

The invention will be explained in more detail by way of the following examples and figures without, however, being restricted thereto.

Figures 1, 2:
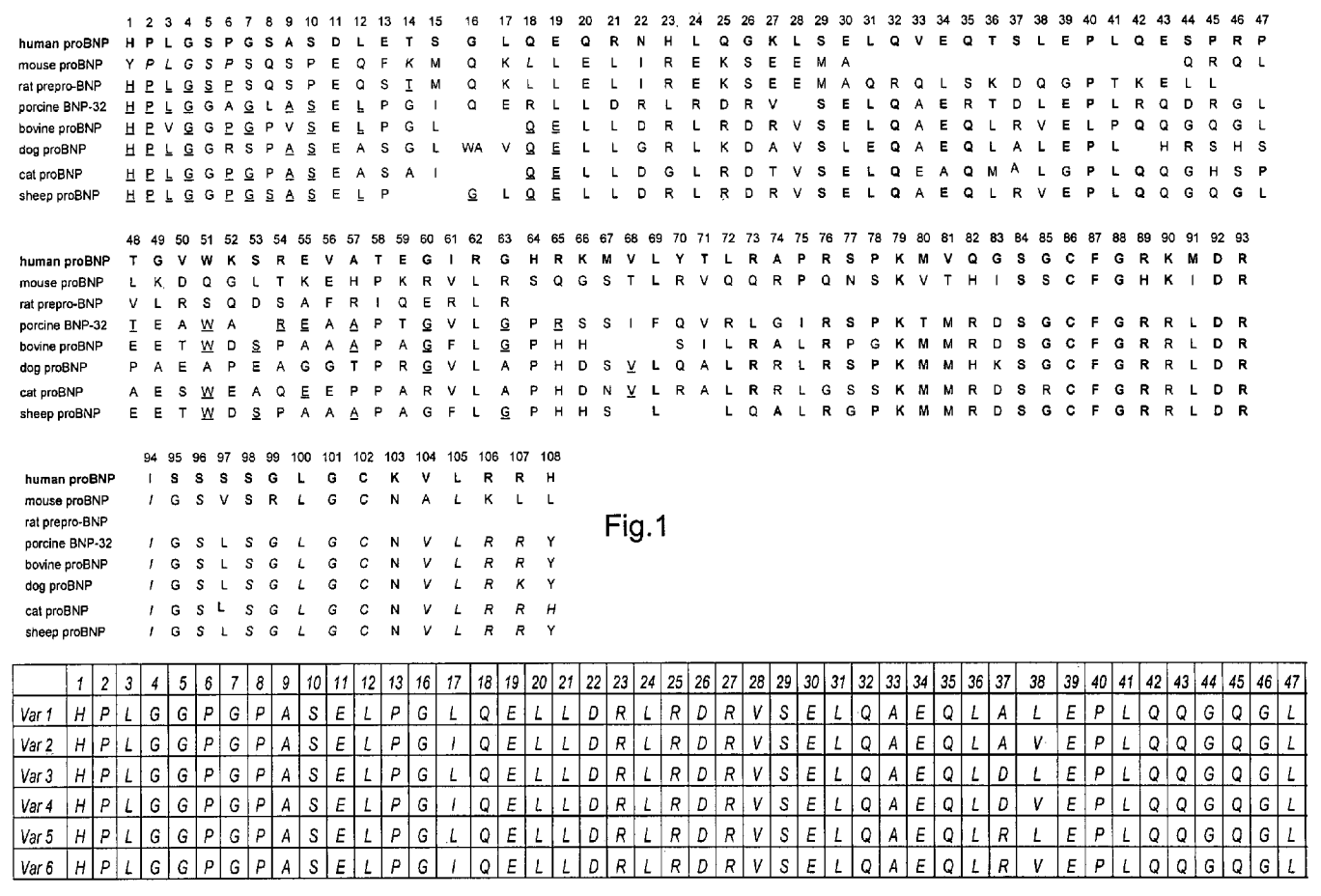

FIG. 1 shows an arrangement of already known BNP-sequences (SEQ ID No. 32-39) of various species;

FIG. 2 shows the design of equine pre-proBNP variants (SEQ ID No. 40-45);

Figure 8:
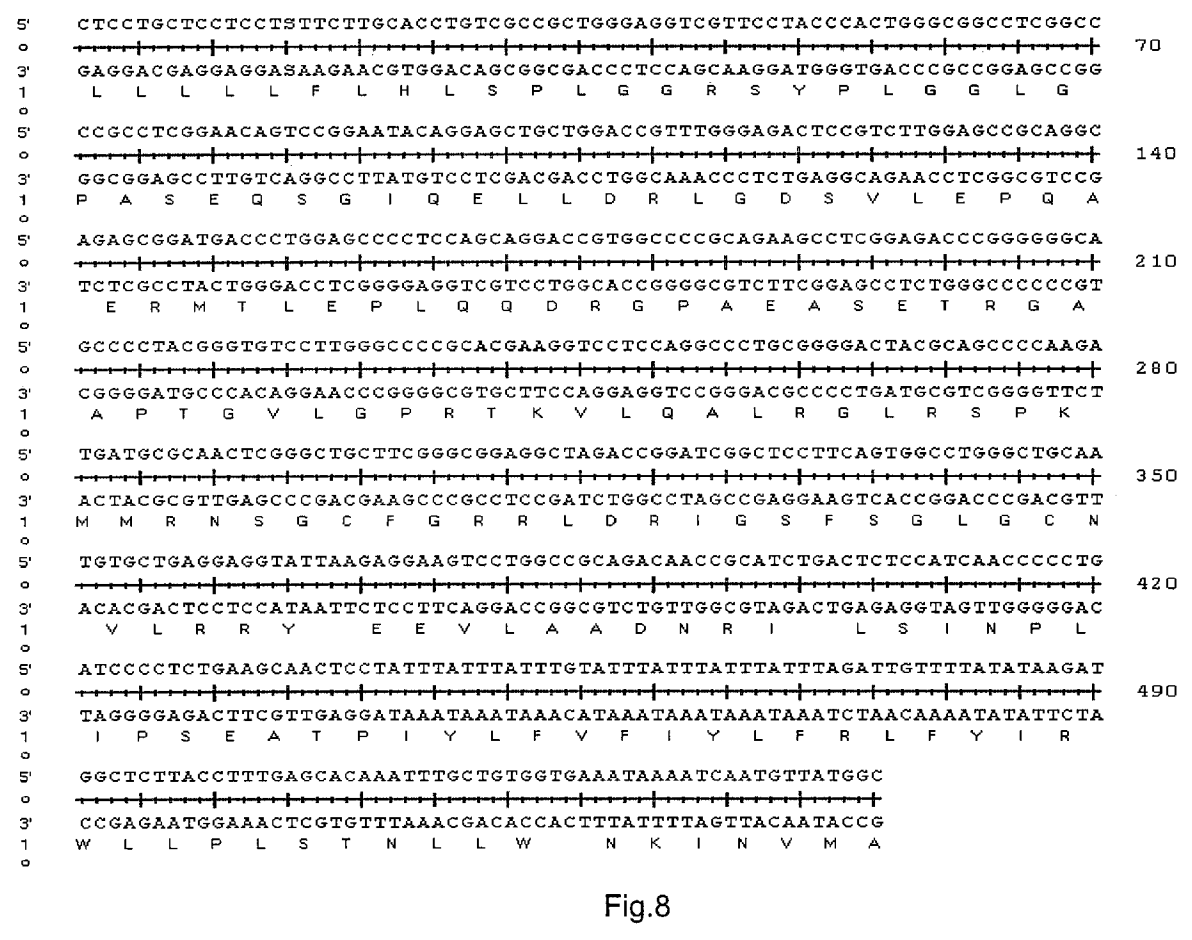

FIG. 8 shows a partial sequence of the cDNA of the pre-pro-BNP from horse (SEQ ID NOs: 46 and 47);

EXAMPLES

Example 1

1. Design of Horse-pre-proBNP Sequences:

Even though the amino acid sequences of those molecules of some species (dog, cat, cattle) which are analogous to human pre-proBNP have already been clarified, no one has so far been able to isolate the pre-proBNP of the horse and to characterise it. This probably is due to the low sequence homology of the pre-proBNP molecules of different animal species (FIG. 1). Therefore, sequences have been developed which could correspond to the amino acid stretches of the pre-proBNPs of the horse. These sequences are not rendered obvious by the previously published sequences of the pre-proBNP molecules of other species since, as has already been mentioned, there is only a slight correlation of these sequences. The choice of the most promising ones of the hypothetical sequence variants (FIG. 2) has been effected by a new approach in which the sequences had been subjected to a molecular analysis by means of proteomic input.

Figure 3:
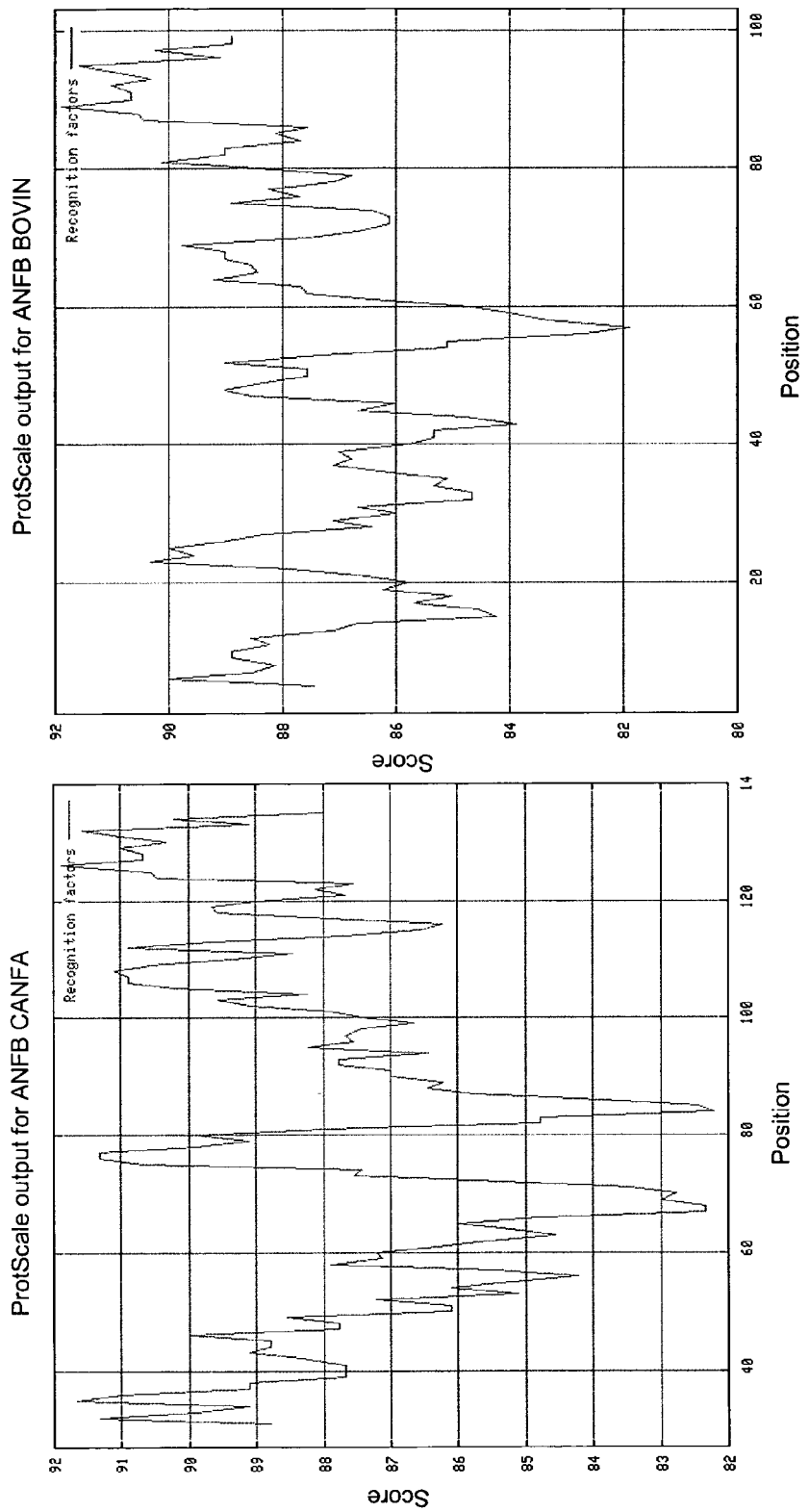
FIG. 3 shows a comparative structural analysis of the pre-proBNPs of various species.
Figure 4:
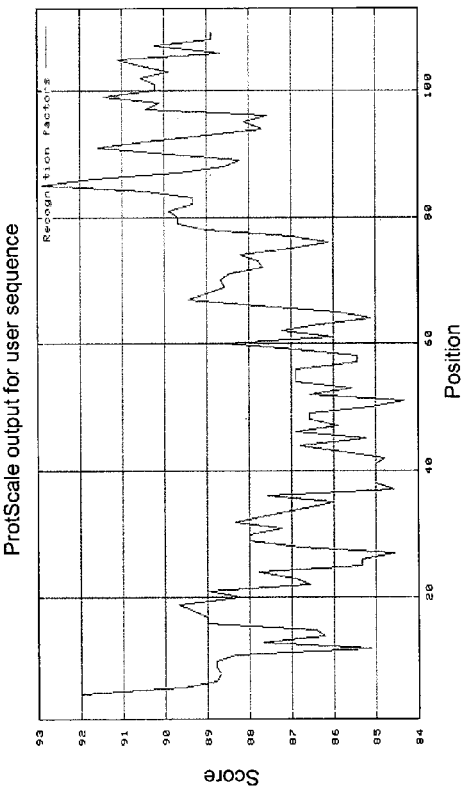
FIG. 4 shows a structural analysis of the most likely variant of the horse-pre-proBNPs (eq-pre-proBNP)

In doing so, some variants of the established sequences in certain regions surprisingly exhibited a significant correlation of the so-called recognition factors which suggested a high structural, and functional, respectively, conservation of these structures and, thus, a high probability for the correctness of the sequence variant. FIG. 3 gives a survey of the molecular analyses carried out. FIG. 4 shows the analogous structural analysis for the most probable sequence variant.

Since the peaks in the recognition factor diagrams correspond to areas with high antigenicity and epitope availability, it has been deduced that antibodies against the regions 1-20 and 45-55 should be suitable for preparing equine eq-pre-proBNPs. Such antibodies were produced and the isolation of the molecule described below was carried out with them.

2. Preparation of Horse-BNP from Serum:

The horse-pre-proBNP is purified by means of immunoaffinity chromatography and detected in a competitive ELISA.

Horse serum was centrifuged for 10 min at 2000 rpm and stored at −20° C. after the addition of 1 ml/l of Proclin300.

Streptavidin-Sepharose (AMERSHAM) was loaded with purified biotinylated S2190 antibody AA 45-55. (Column parameters 100 μg antibody/ml Streptavidin-Sepharose). Elution parameters: binding buffer 0.05 M borate, pH 8.0, elution buffer 0.1 M glycine buffer, pH 2.0, 0.5 ml/min.

Figure 5:
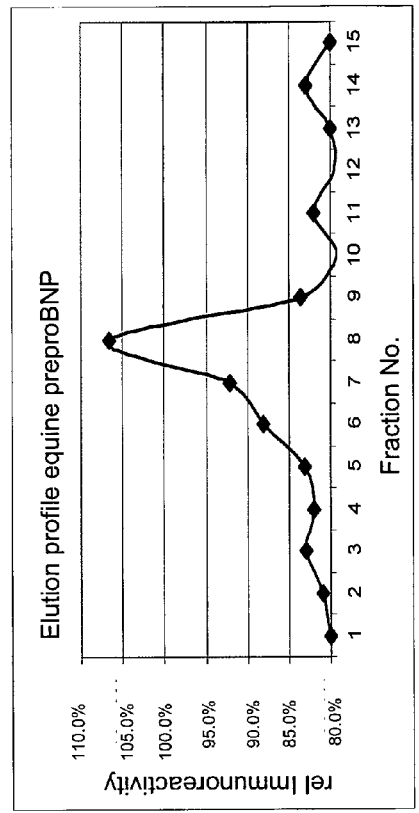
FIG. 5 shows the isolation of eq-pre-proBNP.

3. Detection of eq-pre-proBNP by Means of Competitive ELISA:

The recovered eq-pre-proBNP was detected in an ELISA by using an antibody against sequence 1-20. A peroxidase-labelled peptide of a corresponding sequence was used as tracer molecule. FIG. 5 shows the correlation of the immunoreactivity with the elution profile of the affinity chromatography.

Because of the well-measurable immunoreactivity, it was assumed that eq-pre-proBNP, in fact, had been isolated, and based on the partial sequences determined, a molecular-biological amplification of the eq-pre-proBNP was carried out (4).

4. Amplification of the eq-pre-proBNP from Total-RNA from the Heart Tissue of Horse:

Starting Material:

Two little tubes with heart tissue from horse in RNALater which were denoted by right and left, respectively.

Isolation of Total-RNA:

Isolation of the total-RNA was effected with the RNeasy Fibrous Tissue Midi Kit from Quiagen according to the producer's instructions. 200 mg of tissue each from the left and right half of the heart, respectively, were used for the isolation.

Figure 6:
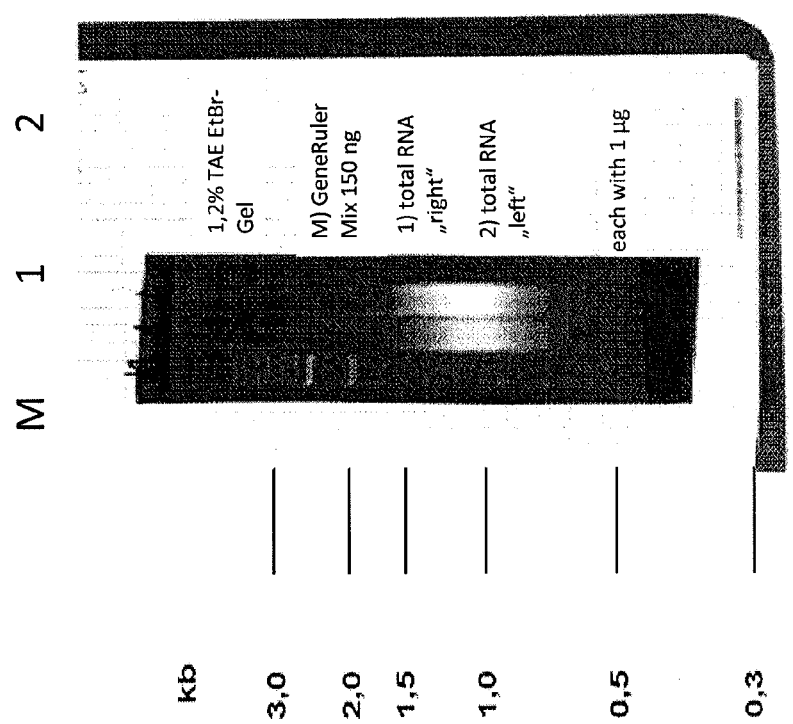
FIG. 6 shows the analysis of the total-RNA on a 1.2% agarose gel: M) GeneRuler DNA Ladder Mix (Fermentas), 150 ng, 1) total-RNA, right half of the heart, 1 µg, 2) total RNA, left half of the heart, 1 µg.

The quality of the total-RNA was analysed on a 1.2% agarose gel (FIG. 6).

cDNA-Synthesis:

The first strand cDNA synthesis was effected with the Library Construction Kit from BD Biosciences according to the producer's instructions. As the template, 1 μg of total-RNA was used. Double-strand cDNA (ds cDNA) was prepared by PCR amplification (15 cycles) with the 5' PCR primer and the CDS III/3' PCR primer.

Figure 7:
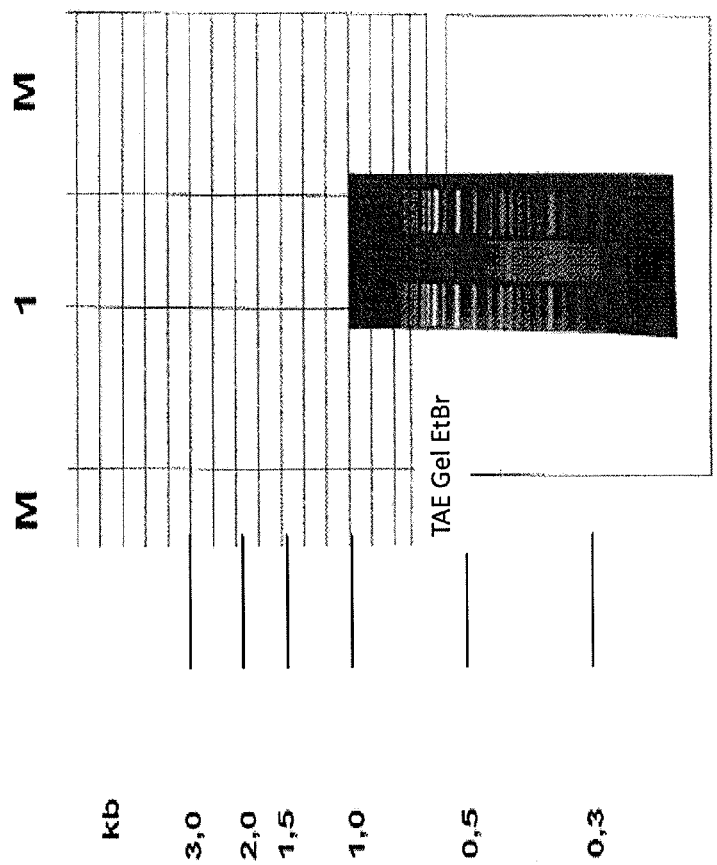
FIG. 7 shows the analysis of the ds cDNA on a 1.2% agarose gel: M) GeneRuler DNA Ladder Mix (Fermentas), 150 ng, 1) ds cDNA from equine heart tissue, 120 ng.

The quality of the ds cDNA was analysed on a 1.2% agarose gel (FIG. 7).

PCR Amplification:

By way of the given reference sequences, several PCR primers were derived. For the amplification of the 3' end of the proBNP gene, gene-specific forward primers and the 3' cDNA synthesis primer were used. For the amplification of the 5' end, gene-specific reverse primers and a primer covering the 3' region of the SMARTIV oligo were used.

Specific PCR products were separated via preparative agarose gels, and the fragments were excised from the gel. Isolation of the DNA was effected with the NucleoSpin Extract II Kit from Macherey-Nagel according to the producer's instructions.

The PCR fragments were each sequenced with the gene-specific primers. The sequence data were trimmed with the program SeqMan (DNAStar Lasergene Software), and the sequences obtained were compared with nucleotide and protein sequences from the Genbank database.

Cloning:

The PCR fragment which exhibited very good homologies to the proBNP sequences was cloned into plasmid pAlli10. The plasmid DNA of several clones was isolated and sequenced. The sequence data were trimmed with the program SeqMan, the vector sequence was removed, and the sequences obtained were assembled. Transcripts of different lengths were identified. This is due to the fact that the transcripts are each polyadenylated at different positions. The resultant consensus sequence corresponds to the shortest transcript and is shown in FIG. 6.

For amplifying the proBNP-specific PCR fragment, a 27mer (5'-CTCCTGCTCCTCCTSTTCTTGCACCTG-3' (SEQ ID No. 18)) was used. The letter S stands for the nucleotides C or G. Both variants have been found in the clones. Therefore, the first 27 nucleotides (nine amino acids) of the obtained sequence cannot be considered to be certain, since they are not predetermined by the primer. Therefore, the derived amino acid sequence of the pre-proBNP from horse can be stated as follows:

```
                                          (Seq. ID. No. 1)
SPLGGRSYPL  GGLGPASEQS  GIQELLDRLG  DSVLEPQAER

MTLEPLQQDR  GPAEASETRG  AAPTGVLGPR  TKVLQALRGL

RSPKMMRNSG  CFGRRLDRIG  SFSGLGCNVL  RRY
```

The equine proBNP sequence reads as follows (the active BNP hormone is underlined); the NT-proBNP sequence therefore consists of the non-underlined portion of SEQ ID NO. 2:

```
                                              (Seq. ID. No. 2)
YPLGGLGPAS EQSGIQELLD RLGDSVLEPQ AERMTLEPLQ

QDRGPAEASE TRGAAPTGVL GPRTKVLQAL RGLRSPKNMR

NSGCFGRRLD RIGSFSGLGC NVLRRY
```

For the amplification of the complete 5' end of the propeptide, 22 sequence-specific reverse primers were synthesized and PCR amplifications were carried out under various conditions. Specific PCR fragments were obtained and sequenced, yet the 5' sequence of the propeptide could not be determined. Maybe the 5' end could not be amplified, since the total RNA showed signs of degradation. Maybe the 5' end of the proBNP has been degraded.

Figure 9:
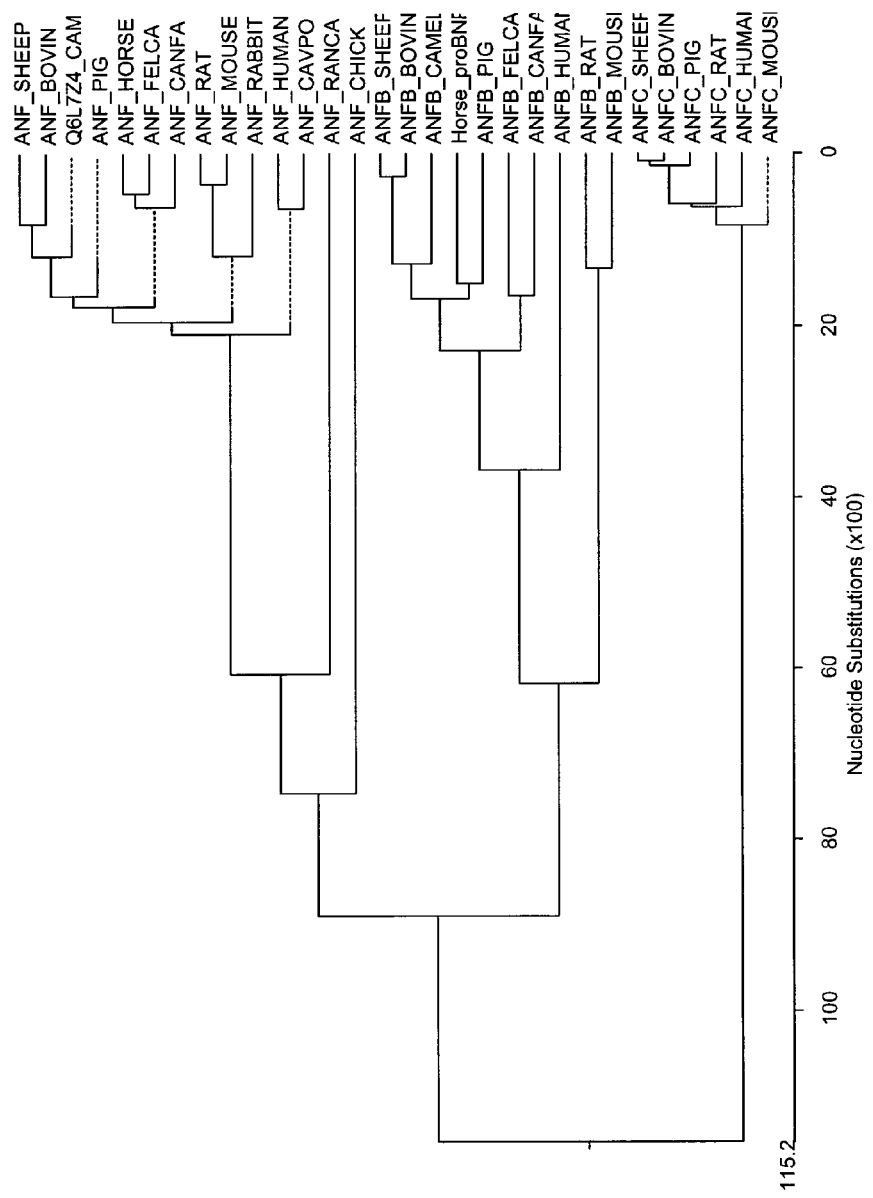
FIG. 9 shows the phylogenetic tree from sequences of various natriuretic peptides; the individual amino acid sequences of the compared natriuretic peptides have been taken from relevant sequence data bases.
Figure 10:
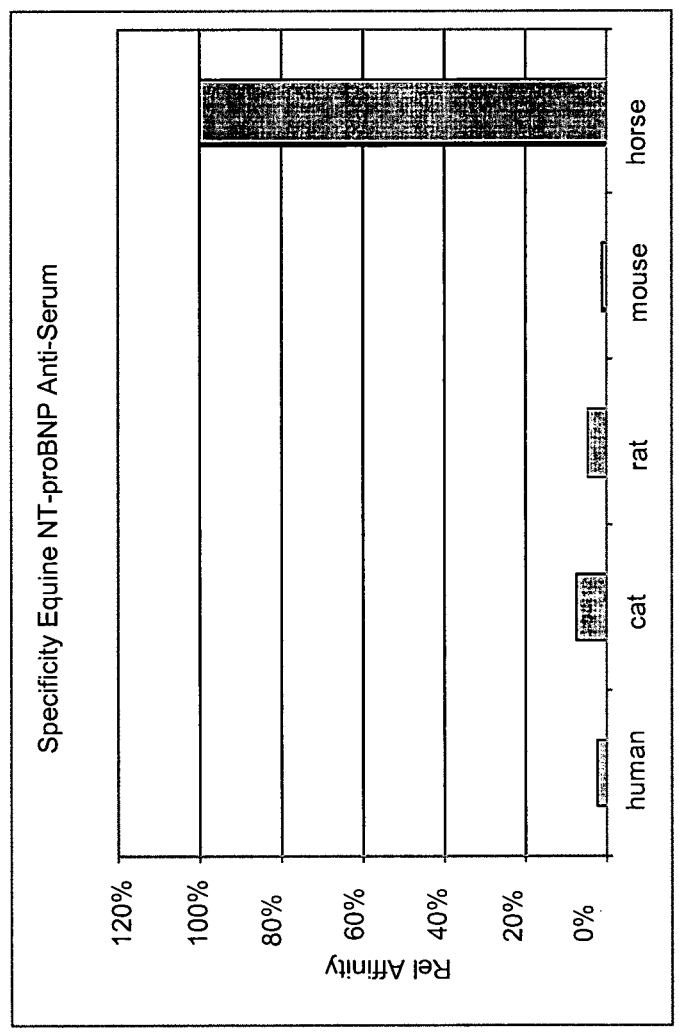
FIG. 10 shows the specificity of an NT-proBNP-anti-serum as opposed to NT-proBNP of various species.

The amino acid sequence according to SEQ ID No. 1 was compared in the program MegAlign (DNAStar Lasergene Software) with various sequences of natriuretic peptides of types A, B and C by means of the ClustalW method. The detected phylogenetic relation of the sequence was illustrated in a phylogenetic tree (cf. FIG. 9). FIG. 9 shows that the proBNP from horse is localized in the cluster of the natriuretic peptides of type B and exhibits the highest homology to the peptide sequence from pig.

5. Specificity of the Antibodies of the Invention:

The specificity of the antibodies of the invention is mainly characterised in that they are capable of distinguishing the equine molecule from the homologues of other known species (humans, mouse, rat, pig, cattle, dog, cat and sheep) via the unique epitopes in equine pre-proBNP.

The specificity with regard to the epitope PLGGLGPASEQS (SEQ ID No. 3) means e.g. that the antibody of the invention binds to this epitope, yet does not bind, or binds with markedly (=e.g. dinstinguishable in the ELISA) less affinity to PLGSPGSASDLE (human) (SEQ ID No. 19), PLGSPSQSPEQF (mouse) (SEQ ID No. 20), PLGSPSQSPEQS (rat) (SEQ ID No. 21), PLGGAGLASELP (pig) (SEQ ID No. 22), PLGGPGPVSELP (cattle) (SEQ ID No. 23), PLGGRSPASEAS (dog) (SEQ ID No. 24), PLGGPGPASEAS (cat) (SEQ ID No. 25) and PLGGPGSASELP (sheep) (SEQ ID No. 26). This holds analogously for the further preferred epitopes PASEQSGIQELL (SEQ ID No. 4), LLDRLGDSVLEP (SEQ ID No. 5), SVLEPQAERMTL (SEQ ID No. 6), PQAERMTLEPLQ (SEQ ID No. 7), EPLQQDRGPAEA (SEQ ID No. 8), LQQDRGPAEASE (SEQ ID No. 9), DRGPAEASETRG (SEQ ID No. 10), PAEASETRGAAP (SEQ ID No. 11), RGAAPTGVLGPR (SEQ ID No. 12), LGPRTKVLQALR (SEQ ID No. 13), PRTKVLQALRGL (SEQ ID No. 14), LQALRGLRSPKM (SEQ ID No. 15), SPKMMRNSGCFG (SEQ ID No. 16) or DRIGSFSGLGCN (SEQ ID No. 17) (each in comparison with the sequences according to FIG. 1). The specific binding to the equine-specific epitopes mentioned here is achieved by the inventive antibodies preferably within the scope of binding to larger polypeptides, primarily to equine pre-proBNP, proBNP, NT-proBNP or BNP.

Example 2

Aim of the Experiment:

Proof of a "species specificity" of the generated sheep antisera for equine NT-proBNP.

Method:

Testing of the reactivity of the equine antisera with NT-proBNP from other species.

Procedure:

Coating of Plates

Recombinant NT-proBNP (1 µg/ml, 200 µg/well, pH 9.6, 0.02 M carbonate buffer) from various species were coated on microtiter plates over night at 4° C. The plates were washed and blocked for 1 h with an blocking buffer solution (10 mM PBS pH 7.4 containing 2% peptone (w/v) and 0.1% (w/v) skim milk powder) for 1 h.

The blocking solution was aspirated, and the plates were dried over night at 30° C.

ELISA-Procedure

Antiserum for equine NT-proBNP was diluted 1:10000 in 0.1 M PBS, pH 7.3, and 200 µl of this solution were applied to the plates that had been coated with recombinant NT-proBNP. After 2 hours of incubation at ambient temperature, the plates were washed, and 200 µl of rabbit-anti-sheep-HRP conjugate were admixed for 30 min. The plates were washed again and incubated with 200 µl of tetramethylbenzidine (TMB) for 10 min. The reaction was stopped with 50 µl 0.1 M sulfuric acid, and the optic density was measured at 450 nm with a standard microplate reading device.

Results:

The reactivity with recombinant NT-proBNP of the following species was tested with the sequences indicated below (human proBNP, SEQ ID No. 27; mouse proBNP, SEQ ID No. 28; rat proBNP, SEQ ID No. 29; cat proBNP, SEQ ID No. 30; horse proBNP, SEQ ID No. 31):

| proBNP | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| human | H | P | L | G | S | P | G | S | A | S | D | L | E | T | S | G | L | Q | E | Q |
| mouse | Y | P | L | G | S | P | S | Q | S | P | E | Q | F | K | M | Q | K | L | L | E |
| rat | H | P | L | G | S | P | S | Q | S | P | E | Q | S | T | M | Q | K | L | L | E |
| cat | H | P | L | G | G | P | G | P | A | S | E | A | S | A | I | | | Q | E | L |
| horse | Y | P | L | G | G | L | G | P | A | S | E | Q | S | | | G | I | Q | E | L |

| | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| human | R | N | H | L | Q | G | K | L | S | E | L | Q | V | E | Q | T | S | L | E | P |
| mouse | L | I | R | E | K | S | E | E | M | A | | | | | | | | | | |
| rat | L | I | R | E | K | S | E | E | M | A | Q | R | Q | L | S | K | D | Q | G | P |
| cat | L | D | G | L | R | D | T | V | S | E | L | Q | E | A | Q | M | A | L | G | P |
| horse | L | D | R | L | G | D | S | V | L | E | P | Q | A | E | R | M | T | L | E | P |

| | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|
| human | L | Q | E | S | P | R | P | T | G | V | W | K | S | R | E | V | A | T | E | G |
| mouse | | | | Q | R | Q | L | L | K | D | Q | G | L | T | K | E | H | P | K | R |

-continued

|       | | | | | | | | | | | | | | | | |
|-------|---|---|---|---|---|---|---|---|---|---|---|---|---|---|---|---|
| rat   | T | K | E | L | L |   | V | L | R | S | Q | D | S | A | F | R | I | Q | E |
| cat   | L | Q | Q | G | H | S | P | A | E | S | W | E | A | Q | E | E | P | P | A | R |
| horse | L | Q | Q | D | R | G | P | A | E | A | S | E | T | R | G | A | A | P | T | G |

|       | 61 | 62 | 63 | 64 | 65 | 66 | 67 | 68 | 69 | 70 | 71 | 72 | 73 | 74 | 75 | 76 |
|-------|----|----|----|----|----|----|----|----|----|----|----|----|----|----|----|----|
| human | I  | R  | G  | H  | R  | K  | M  | V  | L  | Y  | T  | L  | R  | A  | P  | R  |
| mouse | V  | L  | R  | S  | Q  | G  | S  | T  | L  | R  | V  | Q  | Q  | R  | P  | Q  |
| rat   | R  | L  | R  |    |    |    |    |    |    |    |    |    |    |    |    |    |
| cat   | V  | L  | A  | P  | H  | D  | N  | V  | L  | R  | A  | L  | R  | R  | L  | G  |
| horse | V  | L  | G  | P  | R  | T  | K  | V  | L  | Q  | A  | L  | R  | G  | L  | R  |

The relative affinity of the antiserum to the immobilized NT-proBNP molecules was put in relationship to the affinity of the antigen with respect to equine NT-proBNP (affinity to equine NT-proBNP=100%)

|              | human | cat | rat | mouse | horse |
|--------------|-------|-----|-----|-------|-------|
| rel. affinities | 2%    | 7%  | 5%  | 1%    | 100%  |

Conclusion:

The developed sheep-anti-equine-NT-proBNP-antisera were specific, exhibiting only slight cross-reactivity with human, cat, rat or mouse NT-proBNP.

The invention claimed is:

1. A method of determining a presence of equine NT-proBNP (N-terminal form of Brain Natriuretic Peptide), or fragments thereof comprising at least 8 contiguous amino acids from the sequence of amino acid residues 8 to 81 of SEQ ID NO: 1 in an equine sample, comprising:
   providing an equine sample;
   contacting the sample with at least one isolated antibody that specifically binds to equine NT-proBNP and/or to at least one of said fragments thereof; and
   detecting binding of the at least one antibody to the equine NT-proBNP or fragments thereof, thereby determining that the equine NT-proBNP or fragments thereof are present in the sample.

2. The method of claim 1, wherein the at least one antibody specifically binds to at least one specific NT-proBNP-epitope within the sequence of amino acid residues 8 to 81 of SEQ ID NO: 1.

3. The method of claim 2, wherein the NT-proBNP-epitope from SEQ ID NO: 1 is an epitope comprising the sequence PLGGLGPASEQS (SEQ ID NO: 3), PASEQSGIQELL (SEQ ID NO: 4), LLDRLGDSVLEP (SEQ ID NO: 5), SVLEPQAERMTL (SEQ ID NO: 6), PQAERMTLEPLQ (SEQ ID NO: 7), EPLQQDRGPAEA (SEQ ID NO: 8), LQQDRGPAEASE (SEQ ID NO: 9), DRGPAEASETRG (SEQ ID NO: 10), PAEASETRGAAP (SEQ ID NO: 11), RGAAPTGVLGPR (SEQ ID NO: 12), LGPRTKVLQALR (SEQ ID NO: 13), or PRTKVLQALRGL (SEQ ID NO: 14).

4. The method of claim 1, wherein the at least one antibody is polyclonal or monoclonal.

5. The method of claim 1, wherein the at least one antibody is labelled.

6. The method of claim 5, wherein the at least one antibody is labelled with peroxidase, biotin, fluorescent dye, gold colloid or radionuclides.

7. The method of claim 6, wherein the at least one antibody is labelled with horseradish peroxidase.

8. The method of claim 1, wherein the at least one antibody is bound to a solid phase.

9. The method of claim 1, further comprising contacting the sample with at least one isolated anti-NT-proBNP-antibody that binds to equine NT-proBNP but is not specific for equine NT-proBNP.

10. The method of claim 1, further comprising contacting the sample with at least one isolated antibody that is specific to equine pre-proBNP.

11. The method of claim 10, wherein the antibody that is specific to equine pre-proBNP is an antibody that specifically binds to an epitope comprising the sequence SPKMMRNS-GCFG (SEQ ID NO: 16) and/or DRIGSFSGLGCN (SEQ ID NO: 17).

12. The method of claim 1, wherein detecting the binding of the at least one antibody to the equine NT-proBNP or fragments thereof comprises radioimmunoassay, immunobinding assay, Western blot, immunohistochemistry, enzyme-immunoassay, lateral flow device (LFD), or a combination thereof.

13. The method of claim 1, further comprising contacting the at least one antibody that specifically binds to equine NT-proBNP and/or to at least one of said fragments thereof with a polypeptide comprising the amino acid sequence of SEQ ID NO: 1 or the at least one fragment thereof comprising at least 8 contiguous amino acids from the sequence of amino acid residues 8 to 81 of SEQ ID NO: 1 as a positive control or a standard for a concentration determination.

14. The method of claim 1 further comprising determining a concentration of equine NT-proBNP or fragments thereof in the sample.

15. An isolated antibody or an isolated antibody mixture that specifically binds to equine NT-proBNP (N-terminal form of Brain Natriuretic Peptide) or fragments thereof comprising at least 8 contiguous amino acids from the sequence of amino acid residues 8 to 81 of SEQ ID NO: 1.

16. The isolated antibody or isolated antibody mixture of claim 15, wherein the isolated antibody or antibody mixture is further defined as binding to at least one epitope with the sequence comprising PLGGLGPASEQS (SEQ ID NO: 3), PASEQSGIQELL (SEQ ID NO: 4), LLDRLGDSVLEP (SEQ ID NO: 5), SVLEPQAERMTL (SEQ ID NO: 6), PQAERMTLEPLQ (SEQ ID NO: 7), EPLQQDRGPAEA (SEQ ID NO: 8), LQQDRGPAEASE (SEQ ID NO: 9), DRGPAEASETRG (SEQ ID NO: 10), PAEASETRGAAP (SEQ ID NO: 11), RGAAPTGVLGPR (SEQ ID NO: 12), LGPRTKVLQALR (SEQ ID NO: 13), or PRTKVLQALRGL (SEQ ID NO: 14).

17. A kit adapted for determining equine NT-proBNP (N-terminal form of Brain Natriuretic Peptide) or fragments thereof, comprising the at least one antibody or at least one antibody mixture of claim 15 and a polypeptide comprising the amino acid sequence of claim SEQ ID NO: 1 or specific fragment thereof comprising at least 8 contiguous amino acids from the sequence of amino acid residues 8 to 81 of SEQ ID NO: 1.

18. The kit of claim 17, further comprising at least one further antibody that specifically binds to the at least one antibody or that specifically binds to equine NT-proBNP or fragments thereof comprising at least 8 contiguous amino acids from the sequence of amino acid residues 8 to 81 of SEQ ID NO: 1.

19. The kit of claim 17, wherein the at least one antibody is a labelled antibody.

20. The kit of claim 19, wherein the at least one antibody is labelled with peroxidase, biotin, fluorescent dye, gold colloid or radionuclides.

21. An isolated antibody mixture comprising at least one isolated anti-NT-proBNP-antibody that binds to equine NT-proBNP but is not specific for equine NT-proBNP and further comprising an isolated antibody or an isolated antibody mixture that specifically binds to equine NT-proBNP (N-terminal form of Brain Natriuretic Peptide) or fragments thereof comprising at least 8 contiguous amino acids from the sequence of amino acid residues 8 to 81 of SEQ ID NO: 1.

22. The isolated antibody mixture of claim 21, wherein the isolated antibody or antibody mixture that specifically binds to equine NT-proBNP or said fragments thereof is further defined as binding to at least one epitope from SEQ ID NO: 1, further defined as the sequence comprising PLGGLGPASEQS (SEQ ID NO: 3), PASEQSGIQELL (SEQ ID NO: 4), LLDRLGDSVLEP (SEQ ID NO: 5), SVLEPQAERMTL (SEQ ID NO: 6), PQAERMTLEPLQ (SEQ ID NO: 7), EPLQQDRGPAEA (SEQ ID NO: 8), LQQDRGPAEASE (SEQ ID NO: 9), DRGPAEASETRG (SEQ ID NO: 10), PAEASETRGAAP (SEQ ID NO: 11), RGAAPTGVLGPR (SEQ ID NO: 12), LGPRTKVLQALR (SEQ ID NO: 13), or PRTKVLQALRGL (SEQ ID NO: 14).

* * * * *

UNITED STATES PATENT AND TRADEMARK OFFICE
CERTIFICATE OF CORRECTION

PATENT NO.         : 9,103,839 B2                                              Page 1 of 1
APPLICATION NO.    : 12/530122
DATED              : August 11, 2015
INVENTOR(S)        : Woloszczuk et al.

It is certified that error appears in the above-identified patent and that said Letters Patent is hereby corrected as shown below:

In the claims

In claim 17, column 38, line 5, delete "claim" before "SEQ ID No: 1".

Signed and Sealed this
First Day of March, 2016

Michelle K. Lee
*Director of the United States Patent and Trademark Office*